US009629807B2

(12) United States Patent
Arkenau-Maric et al.

(10) Patent No.: US 9,629,807 B2
(45) Date of Patent: *Apr. 25, 2017

(54) ABUSE-PROOFED DOSAGE FORM

(71) Applicant: GRÜNENTHAL GMBH, Aachen (DE)

(72) Inventors: Elisabeth Arkenau-Maric, Cologne (DE); Johannes Bartholomaeus, Aachen (DE); Heinrich Kugelmann, Aachen (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/132,325

(22) Filed: Apr. 19, 2016

(65) Prior Publication Data

US 2016/0263037 A1    Sep. 15, 2016

Related U.S. Application Data

(63) Continuation of application No. 14/875,007, filed on Oct. 5, 2015, now abandoned, which is a continuation of application No. 14/138,372, filed on Dec. 23, 2013, now abandoned, which is a continuation of application No. 13/723,273, filed on Dec. 21, 2012, now abandoned, which is a continuation of application No. 11/462,216, filed on Aug. 3, 2006, now abandoned, which is a continuation-in-part of application No. 11/349,544, filed on Feb. 6, 2006, now Pat. No. 8,075,872, which is a continuation-in-part of application No. 11/348,295, filed on Feb. 6, 2006, now abandoned, which is a continuation-in-part of application No. 10/718,112, filed on Nov. 20, 2003, now Pat. No. 8,114,383.

(30) Foreign Application Priority Data

Aug. 6, 2003  (DE) ................... 10 336 400
Feb. 4, 2005  (DE) .......... 10 2005 005 446

(51) Int. Cl.

| A61K 49/00 | (2006.01) |
|---|---|
| A61K 9/20 | (2006.01) |
| A61K 31/485 | (2006.01) |
| A61J 3/07 | (2006.01) |
| A61K 9/00 | (2006.01) |
| A61K 31/135 | (2006.01) |

(52) U.S. Cl.
CPC ............. *A61K 9/2031* (2013.01); *A61J 3/07* (2013.01); *A61K 9/0092* (2013.01); *A61K 9/2009* (2013.01); *A61K 9/2013* (2013.01); *A61K 9/2027* (2013.01); *A61K 9/2054* (2013.01); *A61K 9/2068* (2013.01); *A61K 9/2072* (2013.01); *A61K 9/2086* (2013.01); *A61K 9/2095* (2013.01); *A61K 31/135* (2013.01); *A61K 31/485* (2013.01); *A61K 9/2004* (2013.01)

(58) Field of Classification Search
CPC .................................................. A61K 9/2031
See application file for complete search history.

(56) References Cited

U.S. PATENT DOCUMENTS

| 2,524,855 A | 10/1950 | Schnider et al. |
|---|---|---|
| 2,806,033 A | 9/1957 | Lewenstein et al. |
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |

(Continued)

FOREIGN PATENT DOCUMENTS

| AR | 046994 A1 | 12/2004 |
|---|---|---|
| AR | 045353 A1 | 10/2005 |

(Continued)

OTHER PUBLICATIONS 2.9 Methoden der pharmazeutischen Technologie, European Pharmacopeia, 143-144, 1997. (Full English translation attached).

Albertini, B. "New spray congealing atomizer for the microencapsulation of highly concentrated solid and liquid substances" European Journal of Pharmaceutics and Biopharmaceutics 69 (2008) 348-357.

Almeida, A. et al., Ethylene vinyl acetate as matrix for oral sustained release dosage forms produced via hot-melt extrusion, European Journal of Pharmaceutics and Biopharmaceutics 77 (2011) 297-305.

(Continued)

*Primary Examiner* — Michael G Hartley
*Assistant Examiner* — Melissa Perreira
(74) *Attorney, Agent, or Firm* — Norris McLaughlin & Marcus, P.A.

(57) ABSTRACT

The invention relates to a dosage form that is thermoformed without discoloration and is safeguarded from abuse, comprising at least one synthetic or natural polymer having a breaking strength of at least 500 N in addition to one or more active substances that could be subject to abuse. The invention also relates to a corresponding method for producing said dosage form.

29 Claims, 2 Drawing Sheets

(56) References Cited

U.S. PATENT DOCUMENTS

| | | |
|---|---|---|
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinty |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | McGinity et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishanamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |

(56) References Cited

U.S. PATENT DOCUMENTS

| | | |
|---|---|---|
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric |
| 8,101,630 B2 | 1/2012 | Kumar et al. |
| 8,114,383 B2 | 2/2012 | Bartholomaeus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomeus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Mari |
| 8,858,963 B1 | 10/2014 | Devarakonda et al. |
| 9,192,578 B2 | 11/2015 | McGinity et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0187192 A1 | 12/2002 | Joshi et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0091630 A1 | 5/2003 | Louie-Helm et al. |
| 2003/0092724 A1 | 5/2003 | Kao et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0185105 A1 | 9/2004 | Berner et al. |
| 2004/0213845 A1 | 10/2004 | Sugihara |
| 2004/0213848 A1 | 10/2004 | Li et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogman et al. |
| 2005/0266084 A1 | 12/2005 | Li et al. |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 4/2008 | Wada et al. |
| 2008/0085304 A1 | 4/2008 | Baichwal et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0280975 A1 | 11/2008 | Badul |

(56) References Cited

U.S. PATENT DOCUMENTS

| | | |
|---|---|---|
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0117191 A1 | 5/2009 | Brown Miller et al. |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0317355 A1 | 12/2009 | Roth et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0159100 A1 | 6/2011 | Anderson et al. |
| 2011/0187017 A1 | 8/2011 | Haupts |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1 | 1/2013 | Schwier et al. |
| 2013/0090349 A1 | 4/2013 | Gei Ler et al. |
| 2013/0129825 A1 | 5/2013 | Billoet et al. |
| 2013/0129826 A1 | 5/2013 | Gei Ler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau Maric et al. |
| 2014/0112989 A1 | 4/2014 | Bartholomäus et al. |
| 2014/0170079 A1 | 6/2014 | Arkenau Maric et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wenig et al. |
| 2015/0030677 A1 | 1/2015 | Adjei et al. |
| 2015/0064250 A1 | 3/2015 | Ghebre-Sellassie et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0374630 A1 | 12/2015 | Arkenau Maric et al. |
| 2016/0256456 A1 | 9/2016 | Caruso et al. |

FOREIGN PATENT DOCUMENTS

| | | |
|---|---|---|
| AR | 049562 A1 | 8/2006 |
| AR | 053304 A1 | 5/2007 |
| AR | 054222 A1 | 6/2007 |
| AR | 054328 A1 | 6/2007 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2006311116 B2 | 1/2013 |
| BR | PI0413318 A | 10/2006 |
| BR | PI0413361 A | 10/2006 |
| BR | PI0513300 A | 5/2008 |
| BR | PI0606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |

(56) References Cited

FOREIGN PATENT DOCUMENTS

| | | | |
|---|---|---|---|
| CN | 1671475 | A | 9/2005 |
| CN | 101022787 | A | 1/2006 |
| CN | 1863513 | A | 11/2006 |
| CN | 1863514 | A | 11/2006 |
| CN | 1917862 | A | 2/2007 |
| CN | 1942174 | A | 4/2007 |
| CN | 101011395 | A | 8/2007 |
| CN | 101027044 | A | 8/2007 |
| CN | 101057849 | A | 10/2007 |
| CN | 101484135 | A | 11/2007 |
| CN | 101091721 | | 12/2007 |
| CN | 101111232 | A | 1/2008 |
| CN | 101175482 | A | 2/2008 |
| CN | 101370485 | A | 2/2009 |
| CN | 101394839 | A | 3/2009 |
| CN | 101652128 | A | 2/2010 |
| DE | 2530563 | A1 | 1/1977 |
| DE | 4229085 | A1 | 3/1994 |
| DE | 4309528 | A1 | 9/1994 |
| DE | 4446470 | A1 | 6/1996 |
| DE | 69400215 | T2 | 10/1996 |
| DE | 19522899 | C1 | 12/1996 |
| DE | 2808505 | A1 | 1/1997 |
| DE | 19753534 | A1 | 6/1999 |
| DE | 19800689 | C1 | 7/1999 |
| DE | 19800698 | A1 | 7/1999 |
| DE | 19822979 | A1 | 12/1999 |
| DE | 69229881 | T2 | 12/1999 |
| DE | 19855440 | A1 | 6/2000 |
| DE | 19856147 | A1 | 6/2000 |
| DE | 19940740 | A1 | 3/2001 |
| DE | 19960494 | A1 | 6/2001 |
| DE | 10036400 | A1 | 6/2002 |
| DE | 69429710 | T2 | 8/2002 |
| DE | 10250083 | A1 | 12/2003 |
| DE | 10250084 | A1 | 5/2004 |
| DE | 10250087 | A1 | 5/2004 |
| DE | 10250088 | A1 | 5/2004 |
| DE | 10336400 | A1 | 3/2005 |
| DE | 10361596 | A1 | 9/2005 |
| DE | 102004019916 | A1 | 11/2005 |
| DE | 102004020220 | A1 | 11/2005 |
| DE | 102004032049 | A1 | 1/2006 |
| DE | 102004032051 | A1 | 1/2006 |
| DE | 102004032103 | A1 | 1/2006 |
| DE | 102005005446 | A1 | 8/2006 |
| DE | 102005005449 | A1 | 8/2006 |
| DE | 102007011485 | A1 | 9/2008 |
| DK | 1658055 | T3 | 7/2007 |
| DK | 1658054 | T3 | 10/2007 |
| DK | 1515702 | T3 | 1/2009 |
| EC | SP066345 | A | 8/2006 |
| EP | 0008131 | A1 | 2/1980 |
| EP | 0043254 | A1 | 1/1982 |
| EP | 0008131 | B1 | 12/1982 |
| EP | 0177893 | A2 | 4/1986 |
| EP | 0216453 | A2 | 4/1987 |
| EP | 0226061 | A2 | 6/1987 |
| EP | 0228417 | A1 | 7/1987 |
| EP | 0229652 | A2 | 7/1987 |
| EP | 0232877 | A2 | 8/1987 |
| EP | 0239973 | A2 | 10/1987 |
| EP | 0240906 | A2 | 10/1987 |
| EP | 0261616 | A2 | 3/1988 |
| EP | 0261616 | A3 | 3/1988 |
| EP | 0270954 | A1 | 6/1988 |
| EP | 0277289 | A1 | 8/1988 |
| EP | 0293066 | A2 | 11/1988 |
| EP | 0328775 | A1 | 8/1989 |
| EP | 0228417 | B1 | 9/1990 |
| EP | 0229652 | B1 | 10/1991 |
| EP | 0477135 | A1 | 3/1992 |
| EP | 0277289 | B1 | 4/1992 |
| EP | 0293066 | B1 | 4/1993 |
| EP | 0270954 | B1 | 5/1993 |
| EP | 0544144 | A1 | 6/1993 |
| EP | 0583726 | A2 | 2/1994 |
| EP | 0598606 | A1 | 5/1994 |
| EP | 0636370 | A1 | 2/1995 |
| EP | 0641195 | A1 | 3/1995 |
| EP | 0647448 | A1 | 4/1995 |
| EP | 0654263 | A1 | 5/1995 |
| EP | 0661045 | A1 | 7/1995 |
| EP | 0675710 | A1 | 10/1995 |
| EP | 0682945 | A2 | 11/1995 |
| EP | 0693475 | A1 | 1/1996 |
| EP | 0820693 | A1 | 1/1996 |
| EP | 0696598 | A1 | 2/1996 |
| EP | 0216453 | B1 | 3/1996 |
| EP | 0583726 | B1 | 11/1996 |
| EP | 0756480 | A1 | 2/1997 |
| EP | 0760654 | A1 | 3/1997 |
| EP | 0761211 | A1 | 3/1997 |
| EP | 0780369 | A1 | 6/1997 |
| EP | 0785775 | A1 | 7/1997 |
| EP | 0809488 | A1 | 12/1997 |
| EP | 0820698 | A1 | 1/1998 |
| EP | 0820753 | A2 | 1/1998 |
| EP | 0857062 | A2 | 8/1998 |
| EP | 0864324 | A1 | 9/1998 |
| EP | 0864326 | A2 | 9/1998 |
| EP | 0598606 | B1 | 6/1999 |
| EP | 0675710 | B1 | 8/1999 |
| EP | 0980894 | A1 | 2/2000 |
| EP | 0988106 | A1 | 3/2000 |
| EP | 1014941 | A1 | 7/2000 |
| EP | 1070504 | A1 | 1/2001 |
| EP | 1127871 | A1 | 8/2001 |
| EP | 1138321 | A2 | 10/2001 |
| EP | 1152026 | A1 | 11/2001 |
| EP | 1138321 | A3 | 1/2002 |
| EP | 1166776 | A2 | 1/2002 |
| EP | 1201233 | A1 | 5/2002 |
| EP | 0661045 | B1 | 7/2002 |
| EP | 1250045 | A2 | 10/2002 |
| EP | 1251120 | A1 | 10/2002 |
| EP | 1293127 | A2 | 3/2003 |
| EP | 1293195 | A1 | 3/2003 |
| EP | 1293196 | A2 | 3/2003 |
| EP | 1127871 | B1 | 9/2003 |
| EP | 1201233 | 61 | 12/2004 |
| EP | 1251120 | B1 | 12/2004 |
| EP | 1492506 | B1 | 1/2005 |
| EP | 1166776 | B1 | 2/2005 |
| EP | 1502592 | A1 | 2/2005 |
| EP | 1658054 | A1 | 2/2005 |
| EP | 1658055 | A1 | 2/2005 |
| EP | 1515702 | B1 | 3/2005 |
| EP | 1527775 | A1 | 4/2005 |
| EP | 1558221 | A1 | 8/2005 |
| EP | 1558257 | A1 | 8/2005 |
| EP | 1560585 | B1 | 8/2005 |
| EP | 1611880 | A2 | 1/2006 |
| EP | 1658054 | B1 | 5/2006 |
| EP | 1138321 | B1 | 1/2007 |
| EP | 1740161 | A2 | 1/2007 |
| EP | 1658055 | B1 | 3/2007 |
| EP | 1765303 | A1 | 3/2007 |
| EP | 1786403 | A1 | 5/2007 |
| EP | 1558221 | B1 | 6/2007 |
| EP | 1842533 | A2 | 10/2007 |
| EP | 1845955 | A1 | 10/2007 |
| EP | 1845956 | A1 | 10/2007 |
| EP | 1859789 | A1 | 11/2007 |
| EP | 1980245 | A1 | 10/2008 |
| EP | 1897545 | A1 | 12/2008 |
| EP | 2131830 | A1 | 12/2009 |
| EP | 2246063 | A1 | 11/2010 |
| EP | 2249811 | A1 | 11/2010 |
| EP | 2273983 | A1 | 1/2011 |
| EP | 2402004 | A2 | 1/2012 |
| ES | 2336571 | T3 | 12/2004 |
| ES | 2260042 | T3 | 11/2006 |
| ES | 2285497 | T3 | 11/2007 |

(56) References Cited

FOREIGN PATENT DOCUMENTS

| | | |
|---|---|---|
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36-022895 | 11/1961 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | 2002524150 A | 8/2002 |
| JP | 2002-275175 A | 9/2002 |
| JP | 2003125706 A | 5/2003 |
| JP | 2003526598 A | 9/2003 |
| JP | 2005506965 A | 3/2005 |
| JP | 2005515152 A | 5/2005 |
| JP | 2005534664 A | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009531453 A | 9/2009 |
| JP | 2009537456 A | 10/2009 |
| JP | 2011504455 A | 2/2011 |
| JP | 2011506493 A | 3/2011 |
| JP | 2013536810 A | 9/2013 |
| JP | 2014505736 A | 3/2014 |
| JP | 2014528437 A | 10/2014 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RS | S55162714 A | 12/1980 |
| RU | 2131244 C1 | 6/1999 |
| RU | 2198197 C2 | 2/2003 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | WO 2004/037259 A1 | 5/2004 |
| TW | 1254634 B | 5/2006 |
| WO | WO 80/00841 A1 | 5/1980 |
| WO | WO 89/05624 A1 | 6/1989 |
| WO | WO 90/03776 A1 | 4/1990 |
| WO | WO 93/06723 A1 | 4/1993 |
| WO | WO 93/10758 A1 | 6/1993 |
| WO | WO 93/10765 A1 | 6/1993 |
| WO | WO 93/11749 A1 | 6/1993 |
| WO | WO 93/23017 A1 | 11/1993 |
| WO | WO 94/06414 A1 | 3/1994 |
| WO | WO 94/08567 A1 | 4/1994 |
| WO | WO 95/17174 A1 | 6/1995 |
| WO | WO 95/20947 A1 | 8/1995 |
| WO | WO 95/22319 A1 | 8/1995 |
| WO | WO 95/30422 A1 | 11/1995 |
| WO | WO 96/00066 A1 | 1/1996 |
| WO | WO 96/03979 A1 | 2/1996 |
| WO | WO 96/14058 A1 | 5/1996 |
| WO | WO 97/00673 A1 | 1/1997 |
| WO | WO 97/33566 A2 | 9/1997 |
| WO | WO 97/49384 A1 | 12/1997 |
| WO | WO 98/35655 A3 | 2/1998 |
| WO | WO 98/20073 A1 | 5/1998 |
| WO | WO 98/28698 A1 | 7/1998 |
| WO | WO 98/35655 A2 | 8/1998 |
| WO | WO 98/51758 A1 | 11/1998 |
| WO | WO 99/12864 A1 | 3/1999 |
| WO | WO 99/32120 A1 | 7/1999 |
| WO | WO 99/44591 A1 | 9/1999 |
| WO | WO 99/45887 A2 | 9/1999 |
| WO | WO 99/48481 A1 | 9/1999 |
| WO | WO 00/13647 A1 | 3/2000 |
| WO | WO 00/33835 A1 | 6/2000 |
| WO | WO 00/40205 A2 | 7/2000 |
| WO | WO 01/08661 A2 | 2/2001 |
| WO | WO 01/12230 A1 | 2/2001 |
| WO | WO 01/15667 A1 | 3/2001 |
| WO | WO 01/52651 A2 | 7/2001 |
| WO | WO 01/58451 A1 | 8/2001 |
| WO | WO 01/97783 A1 | 12/2001 |
| WO | WO 02/26061 A1 | 4/2002 |
| WO | WO 02/26262 A2 | 4/2002 |
| WO | WO 02/26928 A1 | 4/2002 |
| WO | WO 02/35991 A2 | 5/2002 |
| WO | WO 02/071860 A1 | 9/2002 |
| WO | WO 02/088217 A1 | 11/2002 |
| WO | WO 02/094254 A2 | 11/2002 |
| WO | WO 03/006723 A1 | 1/2003 |
| WO | WO 03/013433 A2 | 2/2003 |
| WO | WO 03/013476 A1 | 2/2003 |
| WO | WO 03/013479 A1 | 2/2003 |
| WO | WO 03/013538 A1 | 2/2003 |
| WO | WO 03/015531 A2 | 2/2003 |
| WO | WO 03/018015 A1 | 3/2003 |
| WO | WO 03/024426 A1 | 3/2003 |
| WO | WO 03/024430 A1 | 3/2003 |
| WO | WO 03/026624 A1 | 4/2003 |
| WO | WO 03/026743 A2 | 4/2003 |
| WO | WO 03/028698 A1 | 4/2003 |
| WO | WO 03/028990 A1 | 4/2003 |
| WO | WO 03/031546 A1 | 4/2003 |
| WO | WO 03/035029 A1 | 5/2003 |
| WO | WO 03/035053 A1 | 5/2003 |
| WO | WO 03/035054 A1 | 5/2003 |
| WO | WO 03/035177 A2 | 5/2003 |
| WO | WO 03/039561 A1 | 5/2003 |
| WO | WO 03/049689 A2 | 6/2003 |
| WO | WO 03/053417 A2 | 7/2003 |
| WO | WO 03/068392 A1 | 8/2003 |
| WO | WO 03/070191 A1 | 8/2003 |
| WO | WO 03/092648 A1 | 11/2003 |
| WO | WO 03/094812 A1 | 11/2003 |
| WO | WO 03/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |

(56) References Cited

FOREIGN PATENT DOCUMENTS

| | | |
|---|---|---|
| WO | WO 2004/026280 A2 | 4/2004 |
| WO | WO 2004/037230 A1 | 5/2004 |
| WO | WO 2004/037260 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2008/023261 A1 | 2/2008 |
| WO | WO 2008/033523 A1 | 3/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/128630 A2 | 10/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/059512 A1 | 4/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 A1 | 7/2015 |

OTHER PUBLICATIONS

Almeida, A. et al., Sustained release from hot-melt extruded matrices based on ethylene vinyl acetate and polyethylene oxide, European Journal of Pharmaceutics and Biopharmaceutics 82 (2012) 526-533.

Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.

Apicella A.et al., Biomaterials, vol. 14, No. 2, pp. 83-90, 1993.

Application of a modelling system in the formulation of extended release hydrophilic matrices, Reprinted from Pharmaceutical Technology Europe, Jul. 2006.

Application of Opadry II, complete film coating system, on metformin HCl extended release matrices containing Polyox water soluble resin, Colorcon Apr. 2009.

Arnold C., "Teen Abuse of Painkiller OxyContin on the Rise," www.npr.org, Dec. 19, 2005.

Augustine, R.L., Catalytic Hydrogenation of a, B-Unsaturated Ketones. III The Effect of Quantity and Type of Catalysts, J.Org Chem. 28(1), pp. 152-155, Abstract 1963.

Avis, Kenneth, Parenteral Preparations. Chapter 85. pp. 1518-1541In Remington's Pharmaceutical Sciences, 17th Ed, 1985.

Bailey, F.E., et al., "Some properties of poly(ethylene oxide)' in aqueous solution," Journal of Applied Polymer Science, vol. 1, Issue No. 1, pp. 56-62, 1959.

Bauer et al. Lehrbuch der Pharmazeutischen Technologie, Eight Edition 2006. Stuttgart, pp. 343-352.

Bauer et al. Lehrbuch der Pharmazeutischen Technologie. Sixth Edition 1999. Stuttgart, pp. IX-XV, Table of contents. (Full English translation attached).

(56) References Cited

OTHER PUBLICATIONS

Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al.,"The impact of the addition of naloxone on the use and abuse of pentazocine", Public Health Reports, Jul.-Aug. 1987, vol. 102, No. 4, p. 426-429.
Block, Lawrence. Medicated Applications. Chapter 88. In Remington's Pharmaceutical Sciences, 17th Ed, 1985.
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-free Pharmacokinetics—Standardization of Study Design, Data Anatysis and Reporting" 1999, pp. XI-XIII (table of contents).
Committee for Proprietary Medicinal Products. Note for Guidance on the Investigation of Bioavailability and Bioequivalence. 2001. pp. 1-18.
Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-metl extrusion," Biomaterials 23, 2002, pp. 4241-4248.
Crowley MM, Drug Dev Ind Pharm. Sep. 2007; 33(9):909-26. (Abstract only).
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug abuse, Q.J. Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Dierickx et al., "Co-extrusion as manufacturing technique for fixed-dose combination mini-matrices," European Journal of Pharmaceutics and Biopharmaceutics 81 (2012), 683-689.
Disanto, Anthony. Bioavailability and Bioequivalency Testing. Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, Polyox WSR Solid Dosage Formulation via Melt Extrusion, Feb. 2003, pp. 1-3.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, "The seat of the emetic action of various drugs," J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control. Chapter 83. pp. 1487-1491 In Remington's Pharmaceutical Sciences, 17th Ed, 1985.
Eudragit NE40D web page from Evonik website; downloaded Feb. 24, 2015.
Eudragit RS PO web page from Evonik website; downloaded Feb. 24, 2015.
European Pharmacopeia 5.0; Glyceryl behenate monograph; dated Jan. 2005; downloaded Feb. 24, 2015.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion Application No. 12002708.1-1219, Sep. 24, 2012.
European Search Report and Opinion Application No. 14176277.3-1460, Dec. 15, 2014.
European Search Report and Opinion, Application No. 11006253.6-2112, Dec. 16, 2011.
European Search Report and Opinion, Application No. 11006254.4-2112, Dec. 16, 2011.
European Search Report and Opinion, Application No. 11008131.2-1219, Feb. 24, 2012.
European Search Report and Opinion, Application No. 11009129.5-2112, Apr. 10, 2012.
European Search Report and Opinion, Application No. 12001296.8-1219, Jun. 26, 2012.
European Search Report and Opinion, Application No. 12001301.6-1219, Jun. 26, 2012.
European Search Report and Opinion, Application No. 12003743.7-1219, Sep. 24, 2012.
European Search Report and Written Opinion for EP Application No. 13169658.5, Aug. 6, 2013.
European Search Report and Written Opinion for EP Application No. 13169659.3, Aug. 6, 2013.

(56) References Cited

OTHER PUBLICATIONS

European Search Report and Written Opinion for EP Application No. 13176309.9-1460, Oct. 9, 2013.
European Search Report and Written Opinion for EP Application No. 13197503.9-1460, Feb. 18, 2014.
European Search Report and Written Opinion for EP Application No. 13425151.1-1460, Mar. 11, 2014.
European Search Report and Written Opinion for EP Application No. 14169801.9-1455 Oct. 20, 2014.
Evaluation of Verapamil HCl (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Evonik Rohm GmbH product brochure: Eudragit acrylic polymers for solid oral dosage forms (2009).
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials. Chapter 81. pp. 1473-1477 In Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutical Excipients, 1986, American Pharmaceutical Association, Washington, DC and London (Table of Content Only).
Handbuch der Kunststoff-Extrusionstechnik 1, "Grundlagen" in Chapter 1.2 "Klassifizierung von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
Investigation of a Directly Compressible Metformin HCl 500mg Extended Release Formulation Based on Hypromellose, Colorcon Jul. 2009.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 In Remington's Pharmaceutical Sciences, 17th Ed, 1985.
King, R, "Tablets, Capsules, and Pills" Remington's Pharmaceutical Sciences, pp. 1553-1593, Ch. 89, 1980, $16^{th}$ Edition.
King, Remington's Pharmaceutical Sciences 17th ed., Chapter 78, p. 1418 (1985).
Knevel, Adelbert. Separation. Chapter 78. pp. 1432-1442 In Remington's Pharmaceutical Sciences, 17th Ed, 1985.
Kolter, K., "Compression Behaviour of Kollidon SR," APV/ APGI 2002, Florence, Apr. 11, 2002.
Kondrat, T. , "Technology dosage forms" Moscow 1991, p. 96.
Lee, Y.-S. et al., Principles of Terahertz Science and Technology (Lecture Notes in Physics), Springer; 1 edition 2008. (Table of Contents Only).
Lenindzer, A., "The molecular basis of the structure and functions of cells" Moscow 1974, p. 68.
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990. vol. 2 (Cover and Table of Content only).
Lintner, Carl. Stability of Pharmaceutical Products. Chapter 82. pp. 1478-1486 In Remington's Pharmaceutical Sciences, 17th Ed, 1985.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Phamaceuticals and Health Care Products"; Blackie Academic & Professional; First Edition 1996. (Table of contents only).
Longer et al. Sustained-Release Drug Delivery Systems. Chapter 92. pp. 1611-1661 In Remington's Pharmaceutical Sciences, 17th Ed, 1985.

(56) References Cited

OTHER PUBLICATIONS

Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C.. Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C.W.. Jr. "Degradation of Poly(ethylene Oxide)", Journal of Polymer Science vol. XLVI,1960, pp. 51-57.
McGinity et al., Hot-Melt Extrusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.
Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Miles, R.E. et al., Terahertz Frequency Detection and Identification of Materials and Objects (NATO Science for Peace and Security Series B: Physics and Biophysics), Springer; 1 edition 2007. (Table of contents).
Miller "To crush or not to crush? What to consider before giving medications to a patent with a tube or who has trouble swallowing", Nursing, pp. 50-52, Feb. 2000.
Mises à jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Morissette et al. Advanced Drug Delivery Review 26 (2004), 275-300.
Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; In Remington's Pharmaceutical Sciences, 17th Ed, 1985.
Munjal M. et al., "Polymeric Systems for Amorphous Delta^9-Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Oliveira et al., "Production and characterization of laminar coextrudates at room temperature in the absence of solvents," AAPS Annual Meeting and Exposition, Oct. 14-18, 2012, Chicaso, USA.
Oxicotin: Balancing Risks and Benefits, United States Senate, Hearing, Feb. 12, 2002.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)—Carboxyvinylpolymer Interaction", International Journal of Pharmaceutics, 165, 1998, pp. 239-244.
Ozeki T. et al. "Controlled Release From Solid Dispersion Composed of Poly(ethylene oxide)—Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)—carboxyviylpolymer interpolymer complex by varying molecular wight of poly(ethylene oxide)" Journal of Controlled Release 58, pp. 87-95, 1999.
PCT International Search Report and Written Opinion for PCT Application No. PCT/EP2010/004459 dated Dec. 1, 2010.
PCT International Search Report and Written Opinion for PCT Application No. PCT/EP2009/003290 dated Jul. 9, 2009.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT International Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Sep. 1989, 6(9), S-98.
Pharm. Research, Official Journal of the American Association of Pharmaceutical Scientists, Oct. 1991, 8(10), S-192.
Phillips, G. Briggs. Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release. 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).

(56) References Cited

OTHER PUBLICATIONS

Piringer, O.G.and A.L. Baner, Plastic Packaging: Interactions with Food and Pharmaceuticals, Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf.
Polyox water-soluble resins (Dow Mar. 2002); see http://msds-search.dow.com/PublishedLiteratureDOWCOM/dh_0031/0901b80380031a4a.pdf?filepath=/326-00001.pdf&fromPage=GetDoc).
Polyox WSR-303, retrieved Mar. 10, 2014 from URL http://www.dow.com/dowwolff/en/industrial_solutions/polymers/polyethylene.
Polyox, Colorcon, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms. Chapter 91. pp. 1633-1643 In Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. at al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002, pp. 1-6.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka Ma, Drug Dev Ind Pharm. Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung. 2nd Edition, 2002, Ch 6, pp. 515-519. (Full English translation attached).
Ritschel et al. Die Tablette: Handbuch der Entwicklung, Herstellung und Qualitatssicherung. 2nd Edition, 2002, Ch 6, pp. 69-82 and 115-136.
Ritschel et al. Die Tablette: Handbuch der Entwicklung, Herstellung und Qualitatssicherung. 2nd Edition, 2002, Table of content.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013). pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Salomies et al., "Determination of Oxycodone Hydrochloride in Oral Solutions by High-Performance Thin-Layer Chromatography/Densitometry," Journal of AOAC International, 83: 1497-1501 (2000).
Sax et al., Hawley's Condensed Chemical Dictionary, 11th ed., 1987, p. 1233, definition of "wax".
Scheirs J., et al."Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" The Annals of Pharmacotherapy vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCl From Melt extruded Polyethylene Disks", Pharmaceutical Research, Oct. 1991, vol. 8, No. 10, p. S-192.
Siegel, P. Tonicity, Osmoticity, Osmolality, and Osmolarity. Chapter 80. pp. 1454-1472 In Remington's Pharmaceutical Sciences, 17th Ed, 1985.
Silver, J. "Painkiller OxyContin most commonly abused prescription drug on the streets of Western Pennsylvania", Pittsburg Post-Gazette, Apr. 8, 2001.
Spassov et al., Stereochemistry of Diastereomeric 3-Dialkylaminopropanols Derivatives, and O-Derivatives, J.f. prakt. Chemie, 323:5, 793-800 (1981).
Sprockel O.L et al. "Permeability of Cellulose Polymers: Water Vapour Transmission Rates"., J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., überzogene feste Formen, 1991, 347-68. (English translation attached).
Strang, Abuse of buprenorphie (Temgesic) by snorting, Letter to the editor, British Med. J., 302: 969 (1991).
Stringer J.L., et al "Diffusion of small molecular weight drugs in radiation-crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.

(56) References Cited

OTHER PUBLICATIONS

Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.
Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. pp. 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004: 2 (1): 43-57.
Vippagunta et al. Crystalline Solids, Advanced Drug Delivery Review 48 (2001), 3-26.
Wade and Weller, "Handbook of Pharmaceutical Excipients: 2nd Edition", The American Pharmaceutical Association and the Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart-N.Y., 1982, pp. 82-92 (Full English Translation attached).
Wagner, Pharmazeutische Biologie—Drogen und ihre Inhaltsstoffe—Scharfstoffdrogen, 2nd., revised edition, Gustav Fischer Verlag, Stuttgart-N.Y., 1982,Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", Acta Odontol Scand 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Arm J. Psychiatry, 164(1): pp. 173-174 (2007).
Weiss, U., "Derivatives of Morphine. I 14-Dihydroxydihydromorphinone," J. Am. Chem. Soc. 77, pp. 5891-5892, Nov. 20, 1955.
Wikipedia-Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar-and-pestle grinding on microstructure of sintered alumina gel", Nature 322, pp. 347-349 (Abstract only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmaSciTech 11(2); 910-916 (available on-line May 22, 2010).
Zhang et al., "Properties of Sustained-Release Tablets Prepared by Hot-Melt Extrusion" Pharmaceutical Development and Technology, 1999, 4(2), 241-250.
Bingwen et al, 2008, p. 367. (full translation attached).
Bruce et al, Properties of hot-melt extuded tablet formulations for the colonic delivery of 5-aminosalicylic acid, European Journal of Pharmaceutics and Biopharmaceutics, 59 (2005) 85-97.
Extended European Search Report and Opinion for Application No. EP 15153679.4-1455, Jun. 30, 2015.
Monolithic: retrieved from internet: http:/merriam-webster.com/dictionary/monolithic. Retrieved on Sep. 2, 2015.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
West, Anthony R., Solid state chemistry and its applications, Wiley, New York, 1988, pp. 358 and 365.
Alekseeva et al, Chemical-Pharmaceutical Journal, vol. 41, No. 9, 2007, 49-52. (Full translation attached.).
Cuesov, Drug Production Technology, Khar'kov, 1999, pp. 351-352.
Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.
Efentakis et al, Effects of Excipients on Swellin and Drug Release from Compressed Matrices, in Drug Development and Industrial Pharmacy 23(1):107-112, Jan. 1997, Abstract.
Alekseeva et al, Chemical-Pharmaceutical Journal, vol. 41, No. 9, 2007, 49-52. (English abstract included.)
Borquist et al., "Simulation of the release from a multiparticulate system validated by single pellet and dose release experiements," J. Controlled Release, 97: 453-465 (2004).
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.
Cuesov, 1999, pp. 351-352.
Extended European Search Report and Opinion for Application No. EP 15165064.5-1455, Oct. 16, 2015.
Extended European Search Report and Opinion for Application No. EP 15165065.2-1455, Nov. 2, 2015.

(56) References Cited

OTHER PUBLICATIONS

Extended European Search Report and Opinion for Application No. EP 15165067.8-1455, Nov. 2, 2015.
Extended European Search Report and Opinion for Application No. EP 15165069.4-1455, Nov. 2, 2015.
Extended European Search Report and Opinion for Application No. EP 15165070.2-1455, Nov. 2, 2015.
Extended European Search Report and Opinion for Application No. EP 15184634.2-1455, Mar. 3, 2016.
Saleem et al. "Formulation and Evaluation of Tramadol hydrochloride Rectal Suppositories," Indian J. Pharm Sci. Sep.-Oct. 2008; 70(5), 640-644.
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sidhu et al., "Watch for nonpsychotropics causing psychiatric side effects," Current Psychiatry, vol. 7, No. 4, 2008, 61-74.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
Vynckier et al.,"Hot-melt co-extrusion for the production of fixed-dose combination products with a controlled release ethylcellulose matrix core," International Journal of Pharmaceutics 464 (2014), 65-74.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
U.S. Court of Appeals, Federal Circuit, *Purdue Pharma L.P.* v. *Epic Pharma, LLC*, 117 USPQ2d 1733 (Fed. Cir. 2016).
Decision of the United States District Court for the Southern District of New York, in In re *Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in In re Oxycontin Antitrust Litigation, *Purdue Pharma LP* v. *Teva Pharmaceuticals*, Findings of Fact and Conclusions of Law, District Judge Sidney H. Stein, New York, New York, Jan. 14, 2014.
Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M.et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, Tastes in and Tastes of Paprika, in Taste: Proceedings of the Oxford Symposium on Food and Cookery 28 (Tom Jaine Ed. 1988).
Baumann, T., "Pain Management," Pharmacotherapy: A Pathophysiologic Approach (J.T. DiPiro et al. eds., McGraw-Hill 4th ed. 1999), Ch. 56, 1014-1026.

Baumrucker, S.J., "OxyContin, the Media, and Law Enforcement", American Journal of Hospice & Palliative Care, 18: 154-156 (May/Jun. 2001).
Choi, S. et al, "Hydrophilic Matrix Formulations of Dihydrocodeine Bitartrate with Polyethylene Oxide by Direct Compression," Proceedings of the 29$^{th}$ Annual Meeting of the Controlled Release Society, in collaboration with the Korea Society for Biomaterials, Minneapolis, 1$^{st}$ Edition, 2002, 984-985.
Choi, S.U., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta. Feb. 26, 2013.
Crowley M. et al. Pharmaceutical Applications of Hot-Melt Extrusion: Part I. Drug Dev. & Indus. Pharmacy (2007) 33:909-926.
Crowley M., "Physicochemical and Mechanical Characterization of Hot-Melt Extruded Dosage Forms." Dissertation presented to the Faculty of the Graduate School of the University of Texas at Austin. (May 2003).
Crowley, M. et al., "Properties of Hot-Melt Extruded CPM Tablets Using Hydrophilic Polymers," poster presentation, (2000).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
Crowley0000001-Crowley0000127.
Davies, N. "Sustained Release and Enteric Coated NSAIDs: Are They Really GI Safe?"J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: Polyox(TM) Wsr 30" (effective date: Sep. 18, 2001).
Dow, "Polyox Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc.* v. *Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).

(56) References Cited

OTHER PUBLICATIONS

Jaffe, S.L., "Failed Attempts At Intranasal Abuse of Concerta," Letters to the Editor, J. Am. Acad. Child Adolesc. Psychiatry, 41:1 (Jan. 2002).

Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.

Joint Claim Construction and Prehearing Statement, dated Jul. 11, 2014. *Janssen Pharmaceuticals, Inc. and Grünenthal GMBH v. Actavis Elizabeth LLC and Alkem Laboratories Limited,* Civil Action No. 2:13-cv-04507 CCC-MF (D.N.J.), *Janssen Pharmaceuticals, Inc. and Grünenthal GMBH v. Roxane Laboratories, Inc.,* Civil Action No. 2:13-cv-06929 CCC-MF (D.N.J.), and *Janssen Pharmaceuticals, Inc. and Grünenthal GMBH v. Alkem Laboratories Limited,* Civil Action No. 2:13-cv-07803 CCC-MF (D.N.J.).

Kibbe, Coloring Agents, in Handbook of Pharmaceutical Excipients (3d ed. 2000).

Kidokoro, M. et al. ,"Properties of Tablets Containing Granulations of Ibuprofen and Acrylic Copolymers Prepared by Thermal Processes," Pharm Dev. and Tech. , 6:263-275 (2001).

Kinjo, N. et al, "Antiplasticization in the Slightly Plasticized Poly(vinyl chloride)," Polymer Journal 4(2):143-153 (1973).

Larhib, H. et al., "Compressing polyethyelene glycols: the effect of compression pressure and speed," Int 'l J Pharmaceutics (1997) 147: 199-205.

Lieberman, H., et al., Pharmaceutical Dosage Forms: Tablets, vol. 2, Ch. 5: Granulation Technology and Tablet Characterization (1990), Table of contents and 245-348.

Lyons et al., "Twitch Interpolation in the Assessment of the Maximum Force-Generating Capacity of the Jaw-Closing Muscles in Man," Arch. Oral. Biol. 41:12, 1161-1168 (1996).

Makki, A, et. Al., Eds., A Dictionary of American Idioms, 4th Ed. Barron's, New York (2004), 342-343.

Markovitz, H., et al. "Calculations of Entanglement Coupling Spacings in Linear Polymers." Journal of Physical of Chemistry, 1962. 66(8): 1567-1568.

McCrum, N., et al., Principles of Polymer Engineering. 2nd ed., New York: Oxford University Press. 447(1997), Chapter 7, 296-351.

McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.

McQuay, H. et a. "Methods of Therapeutic Trials," Textbook of Pain 1125-1138 (P.D. Wall & R. Melzack eds., Elsevier 4th ed. 1999), Table of Contents and 1125-1138.

Miura et al., "Comparison of Maximum Bite Force and Dentate Status Between Healthy and Frail Elderly Persons," J. Oral Rehabilitation, vol. 28 (2001), pp. 592-595.

Miyagawa, Y. et al., "Controlled-release of diclofenac sodium from wax matrix granulate," Int 'l J. Pharmaceutics (1996) 138:215-224.

National Drug Intelligence Center Information Bulletin "OxyContin Diversion and Abuse" Jan. 2001.

Payne, H. et al., Denatonium Benzoate as a Bitter Aversive Additive in Ethylene Glycol and Methanol-Based Automotive Products, SAE Technical Paper 930589, Abstract (1993).

Pilpel, N., et al. "The effect of temperature on the tensile strength and disintegration of paracetamol and oxytetracylcine tablets," J Pharm Pharmac., 29:389-392 (1977).

Polyox Water-Soluble Resins NF in Pharmaceutical Applications, Dow Chemical Company, Aug. 2002.

Purdue Pharma LP Material Safety Data Sheet, OxyContin Tablets, 10 mg, 15 mg, 20 mg, 30 mg, 40 mg, 60 mg, Version 16—Sep. 10; available at www.purduephruma.com/msdss/oxycontin_msds.pdf.

Rauwendaal, Chris, PHD, Responsive Expert Report of Chris Rauwendaal, Ph.D. Regarding Expert Report of Michael M. Crowley, Ph.D., dated Jul. 17, 2015.

Repka, M. et al. Pharmaceutical Applications of Hot-Melt Extrusion: Pail II. Drug Dev. & Indus. Pharmacy (2007) 33:1043-1057.

Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.

Seitz, J.A.; et al., "Evaluation of the Physical Properties of Compressed Tablets 1: Tablet Hardness and Friability," J. of Pharm. Sci. , 54:1353-1357 (1965).

Shah, et al., "Some Effects of Humidity and Heat on the Tableting Properties of Microcrystalline Cellulose Formulations 1," J. of Pharm. Sci., 57:181-182 (1967).

Singhal, et al., Handbook of Indices of Food Quality and Authenticity (1997), "Capsicum" p. 398-299.

Smith, K.L. et al. "High Molecular Weight Polymers of Ethylene Oxide—Plastic Properties." Industrial and Engineering Chemistry, 1958. 50(1): 12-16.

Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.

Tiwari, D., et al., "Evaluation of polyoxyethylene homopolymers for buccal bioadhesive drug delivery device formulations." AAPS Pharmsci, 1999. 1(3): Article 13.

Wilkins, J.N., "Pharmacotherapy of Schizophrenia Patients with Comorbid Substance Abuse," Schizophrenia Bulletin, 23:215-228 (1997).

World Health Org., Cancer Pain Relief With a Guide to Opioid Availability (2d ed. 1996).

Yin, T.P., et al., "Viscoelastic Properties of Polyethylene Oxide in Rubber-Like State." Journal of Physical Chemistry, 1961. 65(3): 534-538.

Zacny, J. et al. Drug & Alcohol Dependence (2003) 69:215-232.

Zhang, F., "Hot-Melt Extrusion as a Novel Technology to Prepare Sustained-Release Dosage Forms," Dissertation University of Texas at Austin, Dec. 1999.

Extended European Search Report for Application No. EP 16183922.0-1460, Oct. 31, 2016.

Fathima, N. et al. "Drug-excipient interaction and its importance in dosage form development," Journal of Applied Pharmaceutical Science 01 (06); 2011, pp. 66-71.

Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.

Remington, Chapter 45, pp. 996-1035. 2004.

Schilling, et al., "Novel application of hot-melt extrusion for the preparation of monolithic matrices containing enteric-coated particles." International Journal of Pharmaceutics 400 (2010) 34-31.

Starch 1500, Partially Pregelatinized Maize Starch, technical data from Colorcon, Feb. 2016, 6 pages.

ABUSE-PROOFED DOSAGE FORM

CROSS REFERENCE TO RELATED APPLICATIONS

This application is a Continuation of pending U.S. patent application Ser. No. 14/875,007, filed Oct. 5, 2015, which is a Continuation of U.S. patent application Ser. No. 14/138,372, filed Dec. 23, 2013, now abandoned, which is a Continuation of Ser. No. 13/723,273, filed Dec. 21, 2012, now abandoned, which is a Continuation of U.S. patent application Ser. No. 11/462,216, filed Aug. 3, 2006, now abandoned, which is a Continuation-in-Part-Application of U.S. patent application Ser. No. 11/349,544 filed on Feb. 6, 2006, now U.S. Pat. No. 8,075,872, a Continuation-in-Part-Application of U.S. patent application Ser. No. 11/348,295, filed on Feb. 6, 2006, now abandoned, and a Continuation-in-Part-Application of U.S. patent application Ser. No. 10/718,112 filed on Nov. 20, 2003, now U.S. Pat. No. 8,114,383, and claims priority of German Patent Application No. 10 2005 005446.3 filed on Feb. 4, 2005 and German Patent Application No. 10 336 400.5 filed on Aug. 6, 2003.

BACKGROUND OF THE INVENTION

The present invention relates to an abuse-proofed dosage form thermoformed by extrusion without discoloration and containing, in addition to one or more active ingredients with abuse potential (A) optionally together with physiologically acceptable auxiliary substances (B), at least one synthetic or natural polymer (C) and optionally at least one wax (D), wherein the dosage form exhibits a breaking strength (=resistance to crushing) of at least 500 N, and to a process for the production of the dosage form according to the invention.

Many pharmaceutical active ingredients, in addition to having excellent activity in their appropriate application, also have abuse potential, i.e. they can be used by an abuser to bring about effects other than those intended. Opiates, for example, which are highly active in combating severe to very severe pain, are frequently used by abusers to induce a state of narcosis or euphoria.

In order to make abuse possible, the corresponding dosage forms, such as tablets or capsules are comminuted, for example ground in a mortar, by the abuser, the active ingredient is extracted from the resultant powder using a preferably aqueous liquid and the resultant solution, optionally after being filtered through cotton wool or cellulose wadding, is administered parenterally, in particular intravenously. An additional phenomenon of this kind of administration, in comparison with abusive oral administration, is a further accelerated increase in active ingredient levels giving the abuser the desired effect, namely the "kick" or "rush". This kick is also obtained if the powdered dosage form is administered nasally, i.e. is sniffed. Since controlled-release dosage forms containing active ingredients with abuse potential do not give rise to the kick desired by the abuser when taken orally even in abusively high quantities, such dosage forms are also comminuted and extracted in order to be abused.

U.S. Pat. No. 4,070,494 proposed adding a swellable agent to the dosage form in order to prevent abuse. When water is added to extract the active ingredient, this agent swells and ensures that the filtrate separated from the gel contains only a small quantity of active ingredient.

The multilayer tablet disclosed in WO 95/20947 is based on a similar approach to preventing parenteral abuse, said tablet containing the active ingredient with abuse potential and at least one gel former, each in different layers.

WO 03/015531 A2 discloses another approach to preventing parenteral abuse. A dosage form containing an analgesic opioid and a dye as an aversive agent is described therein. The color released by tampering with the dosage form is intended to discourage the abuser from using the dosage form which has been tampered with.

Another known option for complicating abuse involves adding antagonists to the active ingredients to the dosage form, for example naloxone or naltexone in the case of opioids, or compounds which cause a physiological defense response, such as for example ipecacuanha (ipecac) root.

However, since in most cases of abuse it is still necessary to pulverize the dosage form comprising an active ingredient suitable for abuse, it is an object of the present invention to complicate or prevent the pulverization preceding abuse of the dosage form using the means conventionally available to a potential abuser.

It is a further object to provide a dosage form for active ingredients with potential for abuse which ensures the desired therapeutic effect when correctly administered, but from which the active ingredients cannot be converted into a form suitable for abuse simply by pulverization.

An additional object is to provide a dosage form with enhanced stability when maintained under adverse conditions.

Yet another object is to provide an extrusion process for the manufacture of dosage forms having enhanced abuse prevention and stability characteristics.

A further object is to provide a dosage form having a surface morphology different from that of the core of the dosage form.

An additional object is to provide a dosage form having a non-uniform morphology in general and in particular a dosage form having a layered morphology, in each case where the composition of the dosage form remains uniform.

SUMMARY OF THE INVENTION

These objects have been achieved by the provision of the abuse-proofed dosage form thermoformed by extrusion without discoloration according to the invention which contains, in addition to one or more active ingredients with abuse potential (A), at least one synthetic or natural polymer (C) optionally at least one wax (D), and optionally at least one physiologically acceptable auxiliary substance (B), wherein the dosage form exhibits a breaking strength of at least 500 N.

The breaking strength of at least 500 N (measured as stated in the specification) means that pulverization of the dosage form is considerably more difficult using conventional means, so considerably complicating or preventing the subsequent abuse.

If comminution is inadequate, parenteral, in particular intravenous, administration cannot be performed safely or extraction of the active ingredient therefrom takes too long for the abuser or there is no "kick" when taken orally, as release is not instantaneous.

As used herein, comminution means pulverization of the dosage form with conventional means which are available to an abuser, such as, for example, a mortar and pestle, a hammer, a mallet or other usual means for pulverization by application of force.

The dosage form according to the invention is thus suitable for preventing parenteral, nasal and/or oral abuse of active ingredients, preferably of pharmaceutical active ingredients, with abuse potential.

The advantageous properties of the dosage form according to the invention, in particular also its mechanical properties, may not automatically be achieved by simply processing components (A), (C), optionally (B) and optionally (D) by means of conventional methods for the preparation of dosage forms. In fact, usually suitable apparatuses must be selected for the preparation and critical processing parameters must be adjusted, particularly pressure/force, temperature and time. Dosage forms exhibiting the desired properties may be obtained only if in the course of the preparation of the dosage form the components are exposed to a sufficient pressure at a sufficient temperature for a sufficient period of time. Thus, although it may be possible to utilize conventional apparatuses, the process protocols usually must be adapted in order to meet the required criteria.

Unlike prior art methods which involve the extrusion of polymers in admixture with pharmaceutically active substances but which fail to provide the dosage forms with the beneficial characteristics according to the present invention because unsuitable extruder types are chosen and/or improper extrusion parameters are adjusted, it has now been discovered that the combination of specific extruder type coupled with herein specified extrusion process parameters provides dosage forms with the enhanced properties disclosed herein.

For example, U.S. Pat. No. 6,488,963 relates to pharmaceutical formulations comprising a hot-melt extrudable mixture of a therapeutic compound and a high molecular weight poly(ethylene oxide). It is disclosed that any commercially available extruder model equipped to handle dry feed and having a solid conveying zone, one or multiple heating zones, and an extrusion die may be used. A single screw extruder is preferred and used in the examples. Besides hot-met extrusion, other equivalent processes such as injection molding, hot dipping, melt casting and compression molding are said to be useful. The pharmaceutical formulations obtained by the extrusion process according to U.S. Pat. No. 6,488,963, however, fundamentally differ from the dosage forms according to the present invention. This becomes directly evident from the further processing of the extrudate of Example 2 of U.S. Pat. No. 6,488,963, which, upon exiting the die, may be chopped to the desired length and then be ground to a powder. According to U.S. Pat. No. 6,488,963, such powders are preferred for oral, buccal, and sublingual administration.

In contrast to the grindable pharmaceutical formulations according to U.S. Pat. No. 6,488,963, it is an essential feature of the dosage forms according to the present invention that they exhibit a breaking strength of at least 500 N thereby preventing them from being ground to a powder. In the preparation of the dosage forms according to the invention, a suitable extruder type has to be chosen and the extrusion parameters have to be properly adjusted in order to achieve a breaking strength of at least 500 N. In general, single screw extruders of the type disclosed in U.S. Pat. No. 6,488,963 are not suitable to produce the dosage forms according to the present invention.

DETAILED DESCRIPTION OF THE INVENTION

Figure 1:
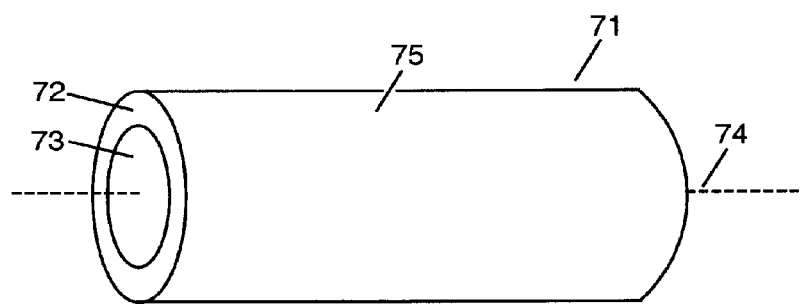
FIG. 1 shows a schematic view of the extrudate of the composition.

Pharmaceutical active ingredients with abuse potential are known to the person skilled in the art, as are the quantities thereof to be used and processes for the production thereof, and may be present in the dosage form according to the invention as such, in the form of the corresponding derivatives thereof, in particular esters or ethers, or in each case in the form of corresponding physiologically acceptable compounds, in particular in the form of the salts or solvates thereof, as racemates or stereoisomers. The dosage form according to the invention is also suitable for the administration of two or more pharmaceutical active ingredients in one dosage form. The dosage form preferably contains just one specific active ingredient.

The dosage form according to the invention is in particular suitable for preventing abuse of a pharmaceutical active ingredient selected from the group consisting of opioids, tranquillizers, preferably benzodiazepines, barbiturates, stimulants and other narcotics.

The dosage form according to the invention is very particularly suitable for preventing abuse of an opioid, tranquillizer or another narcotic selected from the group consisting of N-{1-[2-(4-ethyl-5-oxo-2-tetrazolin-1-yl)ethyl]-4-methoxymethyl-4-piperidyl}propionanilide (alfentanil), 5,5-diallylbarbituric acid (allobarbital), allylprodine, alpha-prodine, 8-chloro-1-methyl-6-phenyl-4H-[1,2,4]triazolo[4,3-a][1,4]-benzodiazepine (alprazolam), 2-diethylaminopropiophenone (amfepramone), (±)-α-methylphenethylamine (amphetamine), 2-(α-methylphenethylamino)-2-phenylacetonitrile (amphetaminil), 5-ethyl-5-isopentylbarbituric acid (amobarbital), anileridine, apocodeine, 5,5-diethylbarbituric acid (barbital), benzylmorphine, bezitramide, 7-bromo-5-(2-pyridyl)-1H-1,4-benzodiazepine-2(3H)-one (bromazepam), 2-bromo-4-(2-chlorophenyl)-9-methyl-6H-thieno[3,2-f][1,2,4]triazolo-[4,3-a][1,4]diazepine (brotizolam), 17-cyclopropylmethyl-4,5a-epoxy-7α[(S)-1-hydroxy-1,2,2-trimethyl-propyl]-6-methoxy-6,14-endo-ethanomorphinan-3-ol (buprenorphine), 5-butyl-5-ethylbarbituric acid (butobarbital), butorphanol, (7-chloro-1,3-dihydro-1-methyl-2-oxo-5-phenyl-2H-1,4-benzodiazepin-3-yl) dimethylcarbamate (camazepam), (1S,2S)-2-amino-1-phenyl-1-propanol (cathine/D-norpseudoephedrine), 7-chloro-N-methyl-5-phenyl-3H-1,4-benzodiazepin-2-ylamine 4-oxide (chlordiazepoxide), 7-chloro-1-methyl-5-phenyl-1H-1,5-benzodiazepine-2,4 (3H,5H)-dione (clobazam), 5-(2-chlorophenyl)-7-nitro-1H-1,4-benzodiazepin-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]diazepin-2(3H)-one (clotiazepam), 10-chloro-11β-(2-chlorophenyl)-2,3,7,11β-tetrahydrooxazolo[3,2-d][1,4]benzodiazepin-6(5H)-one (cloxazolam), (–)-methyl-[3β-benzoyloxy-2β(1αH,5αH)-tropancarboxylate] (cocaine), 4,5α-epoxy-3-methoxy-17-methyl-7-morphinan-6α-ol (codeine), 5-(1-cyclohexenyl)-5-ethylbarbituric acid (cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethylamino-2-methyl-1-phenylpropyl)propionate (dextropropoxyphen), dezocine, diampromide, diamorphone, 7-chloro-1-methyl-5-phenyl-1H-1,4-benzodiazepin-2(3H)-one (diazepam), 4,5α-epoxy- 3-methoxy-17-methyl-6α-morphinanol (dihydrocodeine), 4,5α-epoxy-17-methyl-3,6α-morphinandiol (dihydromorphine), dimenoxadol, dimepheptanol, dimethylthiambutene, dioxaphetyl butyrate, dipipanone, (6αR,10αR)-6,6,9-trimethyl-3-pentyl-6α,7,8,10α-tetrahydro-6H-benzo[c]chromen-1-ol (dronabinol), eptazocine, 8-chloro-6-phenyl-4H-[1,2,4]triazolo[4,3-a][1,4]benzodiazepine (estazolam), ethoheptazine, ethylmethylthiambutene, ethyl [7-chloro-5-(2-fluorophenyl)-2,3-dihydro-2-oxo-1H-1,4-benzodiazepine-3-carboxylate] (ethyl loflazepate), 4,5α-epoxy-3-ethoxy-17-methyl-7-morphinen-6α-ol (ethylmorphine), etonitazene, 4,5α-epoxy-7α-(1-hydroxy-1-methylbutyl)-6-methoxy-17-methyl-6,14-endo-etheno-morphinan-3-ol (etorphine), N-ethyl-3-phenyl-8,9,10-trinorbornan-2-ylamine (fencamfamine), 7-[2-(α-methylphenethylamino)ethyl]-theophylline) (fenethylline), 3-(α-methylphenethylamino)propionitrile (fenproporex), N-(1-phenethyl-4-piperidyl)propionanilide (fentanyl), 7-chloro-5-(2-fluorophenyl)-1-methyl-1H-1,4-benzodiazepin-2(3H)-one (fludiazepam), 5-(2-fluorophenyl)-1-methyl-7-nitro-1H-1,4-benzodiazepin-2(3H)-one (flunitrazepam), 7-chloro-1-(2-diethylaminoethyl)-5-(2-fluorophenyl)-1H-1,4-benzodiazepin-2(3H)-one (flurazepam), 7-chloro-5-phenyl-1-(2,2,2-trifluoroethyl)-1H-1,4-benzodiazepin-2(3H)-one (halazepam), 10-bromo-11β-(2-fluorophenyl)-2,3,7,11μ-tetrahydro[1,3]oxazolyl[3,2-d][1,4]benzodiazepin-6(5H)-one (haloxazolam), heroin, 4,5α-epoxy-3-methoxy-17-methyl-6-morphinanone (hydrocodone), 4,5α-epoxy-3-hydroxy-17-methyl-6-morphinanone (hydromorphone), hydroxypethidine, isomethadone, hydroxymethyl morphinane, 11-chloro-8,12β-dihydro-2,8-dimethyl-12β-phenyl-4H-[1,3]oxazino[3,2-d][1,4]benzodiazepine-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenyl-heptan-3-yl acetate (levacetylmethadol (LAAM)), (−)-6-dimethylamino-4,4-diphenol-3-heptanone (levomethadone), (−)-17-methyl-3-morphinanol (levorphanol), levophenacylmorphane, lofentanil, 6-(2-chlorophenyl)-2-(4-methyl-1-piperazinylmethylene)-8-nitro-2H-imidazo[1,2-a][1,4]-benzodiazepin-1(4H)-one (loprazolam), 7-chloro-5-(2-chlorophenyl)-3-hydroxy-1H-1,4-benzodiazepin-2(3H)-one (lorazepam), 7-chloro-5-(2-chlorophenyl)-3-hydroxy-1-methyl-1H-1,4-benzodiazepin-2(3H)-one (lormetazepam), 5-(4-chlorophenyl)-2,5-dihydro-3H-imidazo[2,1-a]isoindol-5-ol (mazindol), 7-chloro-2,3-dihydro-1-methyl-5-phenyl-1H-1,4-benzodiazepine (medazepam), N-(3-chloropropyl)-α-methylphenethylamine (mefenorex), meperidine, 2-methyl-2-propyltrimethylene dicarbamate (meprobamate), meptazinol, metazocine, methylmorphine, N,α-dimethylphenethylamine (meth-amphetamine), (±)-6-dimethyl-amino-4,4-diphenyl-3-heptanone (methadone), 2-methyl-3-o-tolyl-4(3H)-quinazolinone (methaqualone), methyl [2-phenyl-2-(2-piperidyl)acetate] (methylphenidate), 5-ethyl-1-methyl-5-phenylbarbituric acid (methylphenobarbital), 3,3-diethyl-5-methyl-2,4-piperidinedione (methyprylon), metopon, 8-chloro-6-(2-fluorophenyl)-1-methyl-4H-imidazo[1,5-a][1,4]benzodiazepine (midazolam), 2-(benzhydrylsulfinyl)acetamide (modafinil), 4,5a-epoxy-17-methyl-7-morphinan-3,6α-diol (morphine), myrophine, (±)-trans-3-(1,1-dimethylheptyl)-7,8,10,10α-tetrahydro-1-hydroxy-6,6-dimethyl-6H-dibenzo[-b,d]pyran-9(6αH)-one (nabilone), nalbuphine, nalorphine, narceine, nicomorphine, 1-methyl-7-nitro-5-phenyl-1H-1,4-benzodiazepin-2(3H)-one (nimetazepam), 7-nitro-5-phenyl-1H-1,4-benzodiazepin-2(3H)-one (nitrazepam), 7-chloro-5-phenyl-1H-1,4-benzodiazepin-2(3H)-one (nordazepam), norlevorphanol, 6-dimethylamino-4,4-diphenyl-3-hexanone (normethadone), normorphine, norpipanone, the exudation for the plants belonging to the species *Papaver somniferum* (opium), 7-chloro-3-hydroxy-5-phenyl-1H-1,4-benzodiazepin-2(3H)-one (oxazepam), (cis-trans)-10-chloro-2,3,7,11b-tetrahydro-2-methyl-11b-phenyloxazolo[3,2-d][1,4]benzodiazepin-6-(5H)-one (oxazolam), 4,5α-epoxy-14-hydroxy-3-methoxy-17-methyl-6-morphinanone (oxycodone), oxymorphone, plants and parts of plants belonging to the species *Papaver somniferum* (including the subspecies setigerum), papaveretum, 2-imino-5-phenyl-4-oxazolidinone (pernoline), 1,2,3,4,5,6-hexahydro-6,11-dimethyl-3-(3-methyl-2-butenyl)-2,6-methano-3-benzazocin-8-ol (pentazocine), 5-ethyl-5-(1-methylbutyl)-barbituric acid (pentobarbital), ethyl (1-methyl-4-phenyl-4-piperidine carboxylate) (pethidine), phenadoxone, phenomorphan, phenazocine, phenoperidine, piminodine, pholcodine, 3-methyl-2-phenylmorpholine (phenmetrazine), 5-ethyl-5-phenylbarbituric acid (phenobarbital), α,α-dimethylphenethylamine (phentermine), 7-chloro-5-phenyl-1-(2-propynyl)-1H-1,4-benzodiazepin-2(3H)-one (pinazepam), α-(2-piperidyl)benzhydryl alcohol (pipradrol), 1'-(3-cyano-3,3-diphenylpropyl)[1,4'-bipiperidine]-4'-carboxamide (piritramide), 7-chloro-1-(cyclopropylmethyl)-5-phenyl-1H-1,4-benzodiazepin-2(3H)-one (prazepam), profadol, proheptazine, promedol, properidine, propoxyphene, N-(1-methyl-2-piperidinoethyl)-N-(2-pyridyl)propionamide, methyl {3-[4-methoxycarbonyl-4-(N-phenylpropanamido)-piperidino]propanoate} (remifentanil), 5-sec-butyl-5-ethyl-barbituric acid (secbutabarbital), 5-allyl-5-(1-methylbutyl)-barbituric acid (secobarbital), N-{4-methoxymethyl-1-[2-(2-thienyl)ethyl]-4-piperidyl}-propionanilide (sufentanil), 7-chloro-2-hydroxy-methyl-5-phenyl-1H-1,4-benzodiazepin-2(3H)-one (temazepam), 7-chloro-5-(1-cyclohexenyl)-1-methyl-1H-1,4-benzodiazepin-2(3H)-one (tetrazepam), ethyl (2-dimethylamino-1-phenyl-3-cyclohexene-1-carboxylate) (tilidine (cis and trans)), tramadol, 8-chloro-6-(2-chlorophenyl)-1-methyl-4H-[1,2,4]triazolo[4,3-a][1,4]benzodiazepine (triazolam), 5-(1-methylbutyl)-5-vinylbarbituric acid (vinylbital), (1R,2R)-3-(3-dimethylamino-1-ethyl-2-methyl-propyl)-phenol, (1R,2R,4S)-2-(dimethylamino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclo-hexan-1,3-diol, preferably as racemate, 3-(2-dimethylaminomethyl-1-hydroxy-cyclohexyl)phenyl 2-(4-isobutyl-phenyl)-propionate, 3-(2-dimethylaminomethyl-1-hydroxy-cyclohexyl)phenyl 2-(6-methoxy-naphthalen-2-yl)-propionate, 3-(2-dimethylaminomethyl-cyclohex-1-enyl)-phenyl 2-(4-isobutyl-phenyl)-propionate, 3-(2-dimethylaminomethyl-cyclohex-1-enyl)-phenyl 2-(6-methoxy-naphthalen-2-yl)-propionate, (RR-SS)-2-acetoxy-4-trifluoromethyl-benzoic acid 3-(2-dimethylaminomethyl-1-hydroxy-cyclohexyl)-phenyl ester, (RR-SS)-2-hydroxy-4-trifluoromethyl-benzoic acid 3-(2-dimethylaminomethyl-1-hydroxy-cyclohexyl)-phenyl ester, (RR-SS)-4-chloro-2-hydroxy-benzoic acid 3-(2-dimethylaminomethyl-1-hydroxy-cyclohexyl)-phenyl ester, (RR-SS)-2-hydroxy-4-methyl-benzoic acid 3-(2-dimethylaminomethyl-1-hydroxy-cyclohexyl)-phenyl ester, (RR-SS)-2-hydroxy-4-methoxy-benzoic acid 3-(2-dimethylaminomethyl-1-hydroxy-cyclohexyl)-phenyl ester, (RR-SS)-2-hydroxy-5-nitro-benzoic acid 3-(2-dimethylaminomethyl-1-hydroxy-cyclohexyl)-phenyl ester, (RR-SS)-2',4'-difluoro-3-hydroxy-biphenyl-4-carboxylic acid 3-(2- dimethylaminomethyl-1-hydroxy-cyclohexyl)-phenyl ester and corresponding stereoisomeric compounds, the corresponding derivatives thereof in each case, in particular amides, esters or ethers, and the physiologically acceptable compounds thereof in each case, in particular the salts and solvates thereof, particularly preferably hydrochlorides.

In a preferred embodiment the dosage form according to the invention contains one active substance with abuse potential (A) or more active substance with abuse potentials (A) selected from the group consisting of 1,1-(3-dimethyl-amino-3-phenylpentamethylen)-6-fluor-1,3,4,9-tetrahydro-pyrano[3,4-b]indole, in particular its hemicitrate; 1,1-[3-dimethylamino-3-(2-thienyl)pentamethylen]-1,3,4,9-tetrahydropyrano[3,4-b]indole, in particular its citrate; and 1,1-[3-dimethylamino-3-(2-thienyl)pentamethylen]-1,3,4,9-tetrahydropyrano[3,4-b]-6-fluoro-indole, in particular its hemicitrate. These compounds are known, for example, from WO 2004/043967 or WO 2005/066183. The disclosure of these references is expressly incorporated herein and made a part of this present application.

The amount of the active substance with abuse potential (A), based on the total amount of the dosage form, is preferably within the range from 0.01 to 95 wt.-%, more preferably from 0.5 to 80 wt.-%, still more preferably 1.0 to 70 wt.-%, most preferably 5.0 to 60 wt.-% and in particular 10 to 50 wt.-%. In a preferred embodiment it is more than 20 wt.-%.

The dosage form according to the invention is in particular suitable for preventing abuse of an opioid active ingredient selected from the group comprising oxycodone, hydromorphone, morphine, tramadol and the physiologically acceptable derivatives or compounds thereof, preferably the salts and solvates thereof, preferably the hydrochlorides thereof.

The dosage form according to the invention is furthermore in particular suitable for preventing abuse of an opioid active ingredient selected from the group comprising (1R, 2R)-3-(3-dimethylamino-1-ethyl-2-methyl-propyl)-phenol, (2R,3R)-1-dimethylamino-3-(3-methoxy-phenyl)-2-methyl-pentan-3-ol, (1RS,3RS,6RS)-6-dimethylaminomethyl-1-(3-methoxy-phenyl)-cyclohexane-1,3-diol, (1R,2R)-3-(2-dim-ethylaminoethyl-cyclohexyl)-phenol, the physiologically acceptable salts thereof, preferably hydrochlorides, physiologically acceptable enantiomers, stereoisomers, diastereomers and racemates and the physiologically acceptable derivatives thereof, preferably ethers, esters or amides.

These compounds and processes for the production thereof are described in EP-A-693475 or EP-A-780369. The disclosure of these references is expressly incorporated herein and made a part of this present application.

In order to achieve the necessary breaking strength of the dosage form according to the invention, at least one synthetic or natural polymer (C) is used. The polymer (C) contributes to the breaking strength of the dosage form of at least 500 N, measured using the method disclosed in the specification. At least one polymer selected from the group comprising polyalkylene oxides, preferably polymethylene oxide, polyethylene oxide, polypropylene oxide; polyethylene, polypropylene, polyvinyl chloride, polycarbonate, polystyrene, polyacrylate, copolymers thereof, and mixtures of at least two of the stated polymers is preferably used for this purpose. High molecular weight thermoplastic polyalkylene oxides are preferred. High molecular weight polyethylene oxides with a molecular weight of at least 0.5 million, preferably of at least 1 million up to 15 million, determined by rheological measurements, are particularly preferred. These polymers have a viscosity at 25° C. of 4500 to 17600 cP, measured on a 5 wt. % aqueous solution using a model RVF Brookfield viscosimeter (spindle no. 2/rotational speed 2 rpm), of 400 to 4000 cP, measured on a 2 wt. % aqueous solution using the stated viscosimeter (spindle no. 1 or 3/rotational speed 10 rpm) or of 1650 to 10000 cP, measured on a 1 wt. % aqueous solution using the stated viscosimeter (spindle no. 2/rotational speed 2 rpm).

The polymers are preferably used in powder form. They may be soluble in water.

In order to achieve the necessary breaking strength of the dosage form according to the invention, it is furthermore possible additionally to use at least one natural or synthetic wax (D). The wax (D) contributes to the breaking strength of the dosage form of at least 500 N, measured using the method disclosed in the specification. Waxes with a softening point of at least 60° C. are preferred. Carnauba wax and beeswax are particularly preferred. Carnauba wax is very particularly preferred. Carnauba wax is a natural wax which is obtained from the leaves of the carnauba palm and has a softening point of at least 80° C. When the wax component is additionally used, it is used together with at least one polymer (C) in quantities such that the dosage form has a breaking strength of at least 500 N.

In a preferred embodiment, the breaking strength of the dosage form amounts to at least 500 N, to at least 600 N, to at least 700 N, to at least 800 N, to at least 900 N, to at least 1000 N or even to at least 1100 N.

Component (C) is preferably used in an amount of 20 to 99.9 wt. %, particularly preferably of at least 30 wt. %, very particularly preferably of at least 40 wt. %, relative to the total weight of the dosage form.

In increasingly preferred embodiments, the dosage form according to the invention has a density of at least 0.80 or at least 0.85 g/cm$^3$, at least 0.90 or at least 0.95 g/cm$^3$, at least 1.00, at least 1.05 or at least 1.10 g/cm$^3$, in the range from 0.80 to 1.35 g/cm$^3$, and in particular in the range from 0.95 to 1.25 g/cm$^3$.

The dosage form according to the invention is characterized by a comparatively homogeneous distribution of density. Preferably, the densities of two segments of the dosage form having a volume of 1.0 mm$^3$ each, deviate from one another by not more than ±10%, or by not more than ±7.5%, or by not more than ±5.0%, most preferably not more than ±2.5%, and in particular not more than ±1.0%.

The dosage form according to the invention is characterized by a comparatively homogeneous distribution of the active substance with abuse potential (A). Preferably, the content of component (A) in two segments of the dosage form having a volume of 1.0 mm$^3$ each, deviates from one another by not more than ±10%, more preferably not more than more than ±7.5%, still more preferably not more than ±5.0%, most preferably not more than ±2.5%, and in particular not more than ±1.0%.

Preferably, the total weight of the dosage form according to the invention is within the range from 0.01 g to 1.5 g, more preferably 0.05 g to 1.2 g, still more preferably 0.1 g to 1.0 g, most preferably 0.2 g to 0.9 g and in particular 0.25 g to 0.8 g.

Auxiliary substances (B) which may be used are those known auxiliary substances which are conventional for the formulation of solid dosage forms. These are preferably plasticizers, such as polyethylene glycol, auxiliary substances which influence active ingredient release, preferably hydrophobic or hydrophilic, preferably hydrophilic polymers, very particularly preferably hydroxypropylcellulose, and/or antioxidants. Suitable antioxidants are ascorbic acid, butylhydroxyanisole, butylhydroxytoluene, salts of ascorbic acid, monothioglycerol, phosphorous acid, vitamin C, vitamin E and the derivatives thereof, sodium bisulfite, particularly preferably butylhydroxytoluene (BHT) or butylhydroxyanisole (BHA) and α-tocopherol.

The antioxidant is preferably used in quantities of 0.01 to 10 wt. %, preferably of 0.03 to 5 wt. %, relative to the total weight of the dosage form.

The dosage forms according to the invention are distinguished in that, due their hardness, they cannot be pulverized in conventional comminution means available to an abuser, such as a mortar and pestle. This virtually rules out oral or parenteral, in particular intravenous or nasal abuse. However, in order to prevent any possible abuse of the dosage form according to the invention, the dosage forms according to the invention may, in a preferred embodiment, contain further agents which complicate or prevent abuse as auxiliary substances (B).

The abuse-proofed dosage form according to the invention, which comprises, apart from one or more active ingredients with abuse potential, at least one hardening polymer (C) and optionally at least one wax (D), may accordingly also comprise at least one of the following components (a)-(e) as auxiliary substances (B):

at least one substance which irritates the nasal passages and/or pharynx, at least one viscosity-increasing agent, which, with the assistance of a necessary minimum quantity of an aqueous liquid, forms a gel with the extract obtained from the dosage form, which gel preferably remains visually distinguishable when introduced into a further quantity of an aqueous liquid, at least one antagonist for each of the active ingredients with abuse potential, at least one emetic, at least one dye as an aversive agent, at least one bitter substance.

Components (a) to (f) are additionally each individually suitable for abuse-proofing the dosage form according to the invention. Accordingly, component (a) is preferably suitable for proofing the dosage form against nasal, oral and/or parenteral, preferably intravenous, abuse, component (b) is preferably suitable for proofing against parenteral, particularly preferably intravenous and/or nasal abuse, component (c) is preferably suitable for proofing against nasal and/or parenteral, particularly preferably intravenous, abuse, component (d) is preferably suitable for proofing against parenteral, particularly preferably intravenous, and/or oral and/or nasal abuse, component (e) is suitable as a visual deterrent against oral or parenteral abuse and component (f) is suitable for proofing against oral or nasal abuse. Combined use according to the invention of at least one of the above-stated components makes it possible still more effectively to prevent abuse of dosage forms according to the invention.

In one embodiment, the dosage form according to the invention may also comprise two or more of components (a)-(f) in a combination, preferably (a), (b) and optionally (c) and/or (f) and/or (e) or (a), (b) and optionally (d) and/or (f) and/or (e).

In another embodiment, the dosage form according to the invention may comprise all of components (a)-(f).

If the dosage form according to the invention comprises component (a) to counter abuse, substances which irritate the nasal passages and/or pharynx which may be considered according to the invention are any substances which, when administered via the nasal passages and/or pharynx, bring about a physical reaction which is either so unpleasant for the abuser that he/she does not wish to or cannot continue administration, for example burning, or physiologically counteracts taking of the corresponding active ingredient, for example due to increased nasal secretion or sneezing. These substances which conventionally irritate the nasal passages and/or pharynx may also bring about a very unpleasant sensation or even unbearable pain when administered parenterally, in particular intravenously, such that the abuser does not wish to or cannot continue taking the substance.

Particularly suitable substances which irritate the nasal passages and/or pharynx are those which cause burning, itching, an urge to sneeze, increased formation of secretions or a combination of at least two of these stimuli. Appropriate substances and the quantities thereof which are conventionally to be used are known per se to the person skilled or may be identified by simple preliminary testing.

The substance which irritates the nasal passages and/or pharynx of component (a) is preferably based on one or more constituents or one or more plant parts of at least one hot substance drug.

Corresponding hot substance drugs are known per se to the person skilled in the art and are described, for example, in "Pharmazeutische Biologie—Drogen and ihre Inhaltsstoffe" by Prof. Dr. Hildebert Wagner, 2nd., revised edition, Gustav Fischer Verlag, Stuttgart-New York, 1982, pages 82 et seq. The disclosure of these references is expressly incorporated herein and made a part of this present application.

A dosage unit is taken to mean a separate or separable administration unit, such as for example a tablet or a capsule.

One or more constituents of at least one hot substance drug selected from the group consisting of Allii sativi bulbus (garlic), Asari rhizoma cum herba (Asarum root and leaves), Calami rhizoma (calamus root), Capsici fructus (capsicum), Capsici fructus acer (cayenne pepper), Curcumae longae rhizoma (turmeric root), Curcumae xanthorrhizae rhizoma (Javanese turmeric root), Galangae rhizoma (galangal root), Myristicae semen (nutmeg), Piperis nigri fructus (pepper), Sinapis albae semen (white mustard seed), Sinapis nigri semen (black mustard seed), Zedoariae rhizoma (zedoary root) and Zingiberis rhizoma (ginger root), particularly preferably from the group consisting of Capsici fructus (capsicum), Capsici fructus acer (cayenne pepper) and Piperis nigri fructus (pepper) may preferably be added as component (a) to the dosage form according to the invention.

The constituents of the hot substance drugs preferably comprise o-methoxy(methyl)phenol compounds, acid amide compounds, mustard oils or sulfide compounds or compounds derived therefrom.

Particularly preferably, at least one constituent of the hot substance drugs is selected from the group consisting of myristicin, elemicin, isoeugenol, α-asarone, safrole, gingerols, xanthorrhizol, capsaicinoids, preferably capsaicin, capsaicin derivatives, such as N-vanillyl-9E-octadecenamide, dihydrocapsaicin, nordihydrocapsaicin, homocapsaicin, norcapsaicin and nomorcapsaicin, piperine, preferably trans-piperine, glucosinolates, preferably based on non-volatile mustard oils, particularly preferably based on p-hydroxybenzyl mustard oil, methylmercapto mustard oil or methylsulfonyl mustard oil, and compounds derived from these constituents.

The dosage form according to the invention may preferably contain the plant parts of the corresponding hot substance drugs in a quantity of 0.01 to 30 wt. %, particularly preferably of 0.1 to 0.5 wt. %, in each case relative to the total weight of the dosage unit.

If one or more constituents of corresponding hot substance drugs are used, the quantity thereof in a dosage unit according to the invention preferably amounts to 0.001 to 0.005 wt. %, relative to the total weight of the dosage unit.

Another option for preventing abuse of the dosage form according to the invention consists in adding at least one viscosity-increasing agent as a further abuse-preventing component (b) to the dosage form, which, with the assistance of a necessary minimum quantity of an aqueous liquid, forms a gel with the extract obtained from the dosage form, which gel is virtually impossible to administer safely and preferably remains visually distinguishable when introduced into a further quantity of an aqueous liquid.

For the purposes of the present invention, visually distinguishable means that the active ingredient-containing gel formed with the assistance of a necessary minimum quantity of aqueous liquid, when introduced, preferably with the assistance of a hypodermic needle, into a further quantity of aqueous liquid at 37° C., remains substantially insoluble and cohesive and cannot straightforwardly be dispersed in such a manner that it can safely be administered parenterally, in particular intravenously. The material preferably remains visually distinguishable for at least one minute, preferably for at least 10 minutes.

The increased viscosity of the extract makes it more difficult or even impossible for it to be passed through a needle or injected. If the gel remains visually distinguishable, this means that the gel obtained on introduction into a further quantity of aqueous liquid, for example by injection into blood, initially remains in the form of a largely cohesive thread, which, while it may indeed be broken up into smaller fragments, cannot be dispersed or even dissolved in such a manner that it can safely be administered parenterally, in particular intravenously. In combination with at least one optionally present component (a) to (e), this additionally leads to unpleasant burning, vomiting, bad flavor and/or visual deterrence.

Intravenous administration of such a gel would most probably result in obstruction of blood vessels, associated with serious harm to the health of the abuser.

In order to verify whether a viscosity-increasing agent is suitable as component (b) for use in the dosage form according to the invention, the active ingredient is mixed with the viscosity-increasing agent and suspended in 10 ml of water at a temperature of 25° C. If this results in the formation of a gel which fulfils the above-stated conditions, the corresponding viscosity-increasing agent is suitable for preventing or averting abuse of the dosage forms according to the invention.

If component (b) is added to the dosage form according to the invention, one or more viscosity-increasing agents are used which are selected from the group comprising microcrystalline cellulose containing carboxymethylcellulose sodium (e.g. Avicel® RC 591, FMC Corporation, Philadelphia, Pa., US), carboxymethylcellulose sodium (Blanose® Hercules Inc., Wilmington, US; CMC-Na C300P®, Cesalpinia Food S.p.A., Milano, IT; Frimulsion BLC-5®, Cesalpinia Food S.p.A., Milano, IT; Tylose C300 P® SE Tylose GmbH & Co. KG, Wiesbaden, Del.), polyacrylic acid (Carbopol® 980 NF, Noveon IP Holdings Corp., Cleveland, Ohio, US, Carbopol® 981, Noveon IP Holdings Corp., Cleveland, Ohio, US), locust bean flour (Cesagum® LA-200, Cesalpinia Food S.p.A., Milano, IT; Cesagum® LID/150, Cesalpinia Food S.p.A., Milano, IT; Cesagum® LN-1, Cesalpinia Food S.p.A., Milano, IT), pectins, preferably from citrus fruits or apples (Cesapectin® HM Medium Rapid Set, Cesalpinia Food S.p.A., Milano, IT), waxy maize starch (C*Gel 04201®, Cerestar Deutschland GmbH, Krefeld, Del.), sodium alginate (Frimulsion ALG (E401)®, Cesalpinia Food S.p.A., Milano, IT), guar flour (Frimulsion BM®, Cesalpinia Food S.p.A., Milano, IT; Polygum 26/1-75®, Polygal AG, Märstetten, CH), iota carrageen (Frimulsion D0210, Cesalpinia Food S.p.A., Milano, IT), karaya gum, gellan gum (Kelcogel F®, Kelcogel LT100®, CP Kelco ApS, Lille Skensved, DK), galactomannan (Meyprogat 150 ®, Meyhall Chemical, Kreuzlingen, CH), tara bean flour (Polygum 43/1®, Polygal AG, Märstetten, CH), propylene glycol alginate (Protanal-Ester SD-LB®, FCM Biopolymer AS, Drammen, NO), sodium hyaluronate, tragacanth, tara gum (Vidogum SP 200® Unipektin AG, Zürich, CH), fermented polysaccharide welan gum (K1A96), xanthan gum (Xantural 180®). Xanthans are particularly preferred. The names stated in brackets are the trade names by which the materials are known commercially. In general, a quantity of 0.1 to 20 wt. %, particularly preferably of 0.1 to 15 wt. % of the stated viscosity-increasing agent(s) is sufficient to fulfill the above-stated conditions The component (b) viscosity-increasing agents, where provided, are preferably present in the dosage form according to the invention in quantities of ≥5 mg per dosage unit, i.e. per administration unit.

In a particularly preferred embodiment of the present invention, the viscosity-increasing agents used as component (b) are those which, on extraction from the dosage form with the necessary minimum quantity of aqueous liquid, form a gel which encloses air bubbles. The resultant gels are distinguished by a turbid appearance, which provides the potential abuser with an additional optical warning and discourages him/her from administering the gel parenterally.

Component (C) may also optionally serves as an additional viscosity-increasing agent which, with the assistance of a minimum necessary quantity of an aqueous liquid, forms a gel.

It is also possible to formulate the viscosity-increasing agent and the other constituents in the dosage form according to the invention in a mutually spatially separated arrangement.

In order to discourage and prevent abuse, the dosage form according to the invention may furthermore comprise component (c), namely one or more antagonists for the active ingredient or active ingredients with abuse potential, wherein the antagonists are preferably spatially separated from the remaining constituents of the invention dosage according to the form and, when correctly used, do not exert any effect.

Suitable antagonists for preventing abuse of the active ingredients are known per se to the person skilled in the art and may be present in the dosage form according to the invention as such or in the form of corresponding derivatives, in particular esters or ethers, or in each case in the form of corresponding physiologically acceptable compounds, in particular in the form of the salts or solvates thereof.

If the active ingredient present in the dosage form is an opioid, the antagonist used is preferably an antagonist selected from the group comprising naloxone, naltrexone, nalmefene, nalid, nalmexone, nalorphine or naluphine, in each case optionally in the form of a corresponding physiologically acceptable compound, in particular in the form of a base, a salt or solvate. The corresponding antagonists, where component (c) is provided, are preferably used in a quantity of ≥1 mg, particularly preferably in a quantity of 3 to 100 mg, very particularly preferably in a quantity of 5 to 50 mg per dosage form, i.e. per administration unit.

If the dosage form according to the invention comprises a stimulant as active ingredient, the antagonist is preferably a neuroleptic, preferably at least one compound selected from the group consisting of haloperidol, promethazine, fluphenazine, perphenazine, levomepromazine, thioridazine, perazine, chlorpromazine, chlorprothixine, zuclopentixol, flupentixol, prothipendyl, zotepine, benperidol, pipamperone, melperone and bromperidol.

The dosage form according to the invention preferably comprises these antagonists in a conventional therapeutic dose known to the person skilled in the art, particularly preferably in a quantity of twice to four times the conventional dose per administration unit.

If the combination to discourage and prevent abuse of the dosage form according to the invention comprises component (d), it may comprise at least one emetic, which is preferably present in a spatially separated arrangement from the other components of the dosage form according to the invention and, when correctly used, is intended not to exert its effect in the body.

Suitable emetics for preventing abuse of an active ingredient are known per se to the person skilled in the art and may be present in the dosage form according to the invention as such or in the form of corresponding derivatives, in particular esters or ethers, or in each case in the form of corresponding physiologically acceptable compounds, in particular in the form of the salts or solvates thereof.

An emetic based on one or more constituents of ipecacuanha (ipecac) root, preferably based on the constituent emetine may preferably be considered in the dosage form according to the invention, as are, for example, described in "Pharmazeutische Biologie—Drogen and ihre Inhaltsstoffe" by Prof. Dr. Hildebert Wagner, 2nd, revised edition, Gustav Fischer Verlag, Stuttgart, New York, 1982. The disclosure of these references is expressly incorporated herein and made a part of this present application.

The dosage form according to the invention may preferably comprise the emetic emetine as component (d), preferably in a quantity of $\geq 3$ mg, particularly preferably of $\geq 10$ mg and very particularly preferably in a quantity of $\geq 20$ mg per dosage form, i.e. administration unit.

Apomorphine may likewise preferably be used as an emetic in the abuse-proofing according to the invention, preferably in a quantity of preferably $\geq 3$ mg, particularly preferably of $\geq 5$ mg and very particularly preferably of $\geq 7$ mg per administration unit.

If the dosage form according to the invention contains component (e) as a further abuse-preventing auxiliary substance, the use of a such a dye brings about an intense coloration of a corresponding aqueous solution, in particular when the attempt is made to extract the active ingredient for parenteral, preferably intravenous administration, which coloration may act as a deterrent to the potential abuser. Oral abuse, which conventionally begins by means of aqueous extraction of the active ingredient, may also be prevented by this coloration. Suitable dyes and the quantities required for the necessary deterrence may be found in WO 03/015531. The disclosure of this reference is expressly incorporated herein and made a part of this present application.

If the dosage form according to the invention contains component (f) as a further abuse-preventing auxiliary substance, this addition of at least one bitter substance and the consequent impairment of the flavor of the dosage form additionally prevents oral and/or nasal abuse.

Suitable bitter substances and the quantities effective for use may be found in US-2003/0064099 A1. The disclosure of this reference is expressly incorporated herein and made a part of this present application. Suitable bitter substances are preferably aromatic oils, preferably peppermint oil, eucalyptus oil, bitter almond oil, menthol, fruit aroma substances, preferably aroma substances from lemons, oranges, limes, grapefruit or mixtures thereof, and/or denatonium benzoate (Bitrex®). Denatonium benzoate is particularly preferred.

The solid dosage form according to the invention is suitable to be taken orally, vaginally or rectally, preferably orally. The dosage form is preferably not in film form.

The dosage form according to the invention may assume multiparticulate form, preferably in the form of microtablets, microcapsules, micropellets, granules, spheroids, beads or pellets, optionally packaged in capsules or pressed into tablets, preferably for oral administration. The multiparticulate forms preferably have a size or size distribution in the range from 0.1 to 3 mm, particularly preferably in the range from 0.5 to 2 mm. Depending on the desired dosage form, conventional auxiliary substances (B) are optionally also used for the formulation of the dosage form.

The solid, abuse-proofed dosage form according to the invention is preferably produced by thermoforming with the assistance of an extruder without any observable consequent discoloration of the extrudates.

In order to investigate the extent of discoloration due to this thermoforming, the color of the mixture of starting components of which the dosage form consists is first determined without addition of a color-imparting component, such as for example a coloring pigment or an intrinsically colored component (for example α-tocopherol). This composition is then thermoformed according to the invention, wherein all process steps, including cooling of the extrudate, are preferably performed under an inert gas atmosphere. By way of comparison, the same composition is produced by the same process, but without an inert gas atmosphere. The color of the dosage form produced according to the invention from the starting composition and of the dosage form produced by way of comparison is determined. The determination is performed with the assistance of "Munsell Book of Color" from Munsell Color Company Baltimore, Md., USA, 1966 edition. If the color of the dosage form thermoformed according to the invention has a color with identification no. N 9.5, but at most a color with the identification no. 5Y 9/1, thermoforming is classed as being "without discoloration". If the dosage form has a color with the identification no. 5Y 9/2 or greater, as determined according to the Munsell Book of Color, the thermoforming is classed as being "with discoloration".

Surprisingly, the dosage forms according to the invention exhibit no discoloration classed in accordance with the above classification, if the entire production process is performed under an inert gas atmosphere, preferably under a nitrogen atmosphere with the assistance of an extruder for thermoforming.

In one embodiment of the present invention the abuse-proofed dosage forms are produced by a process comprising mixing components (A), the optionally present component (B), (C) and the optionally present component (D) and co-mixing the optionally present components a) to f) or, if necessary, separately mixing with the addition of component (C) and optionally (D), heating the resultant mixture or the resultant mixtures in the extruder at least up to the softening point of component (C) and extruding the mixture through the outlet orifice of the extruder by application of force, singulating and forming the still plastic extrudate into the dosage form or cooling and forming the extrudate into the dosage form, wherein process steps II) and III) and optionally process steps I) and IV) are optionally performed under an inert gas atmosphere, preferably a nitrogen atmosphere.

Mixing of the components according to process step I) may also proceed in the extruder.

Mixing of components (A), optionally (B), (C) and optionally (D) and of the optionally present further components (a)-(f) and optionally components (C) and the optionally present component (D) may also optionally proceed in a mixer known to the person skilled in the art. The mixer may, for example, be a roll mixer, shaking mixer, shear mixer or compulsory mixer.

Before blending with the remaining components, component (C) and the optionally present component (D) is preferably provided according to the invention with an antioxidant. This may proceed by mixing the two components, (C) and the antioxidant, preferably by dissolving or suspending the antioxidant in a highly volatile solvent and homogeneously mixing this solution or suspension with component (C) and the optionally present component (D) and removing the solvent by drying, preferably under an inert gas atmosphere. Alternatively, a physiologically acceptable auxiliary substance (B) or a wax (D) may serve as the solvent, preferably at elevated temperature. For example, when polyethylene glycol is used as a plasticizer, it may be molten or liquefied at moderately elevated temperature and the antioxidant may be dissolved therein. Under these circumstances the highly volatile solvent can be omitted.

The dosage forms according to the invention which contain subunits with further auxiliary substances which prevent or complicate abuse may be produced by coextruding or separately extruding the mixtures according to step I).

In any event, the, preferably molten, mixture or mixtures which has/have been heated in the extruder at least up to the softening point of component (C) is/are extruded from the extruder through a die with at least one bore.

The process according to the invention is preferably performed using conventional screw extruders, particularly preferably twin-screw-extruders.

The extruder preferably comprises at least two temperature zones, with heating of the mixture at least up to the softening point of component (C) proceeding in the first zone, which is downstream from a feed zone and optionally mixing zone. The throughput of the mixture is preferably from 2.0 kg to 8.0 kg/hour.

After heating at least up to the softening point of component (C), the molten mixture is conveyed with the assistance of the screws, further homogenized, compressed or compacted such that, immediately before emerging from the extruder die, it exhibits a minimum pressure of 5 bar, preferably of at least 10 bar, and is extruded through the die as an extruded strand or strands, depending on the number of bores which the die comprises. The die geometry or the geometry of the bores is freely selectable. The die or the bores may accordingly exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of component (C) and does not rise above a temperature at which the active substance with abuse potential which is to be processed may be damaged. Preferably, the temperature of the mixture to be extruded is adjusted to below 180° C., preferably below 150° C., but at least to the softening temperature of component (C).

In general, the following parameters are critical in extrusion processes and have the consequences described:

1. Throughput (kg Per Hour)

If the throughput is too low the extruder is not correctly filled and the material is stressed thereby affecting the viscosity and the release profile of the final product; if the throughput is too high the load of the extruder is higher than 100% and the extruder shuts down automatically; and if the throughput is tolerable but close to the upper limit significant expansion of the extruded strand occurs (also known as "die swelling").

2. Screw Geometry

A minimum number of kneading elements is required in order to obtain a homogeneous mixture; if the number is too high, the material is stressed thereby affecting the viscosity and the release profile of the final product. The number and lead of the conveying elements influences the homogeneity of the mixture and its residence time in the extruder and controls the increase of the pressure in front of the die. Mixing elements improve the homogeneity of the mixture; and eccentric screw heads allow for a continuous discharge of the extrudate without density variations.

3. Die and Merge Element Geometry

The geometry of the element which merges the extrusion strands in front of the die, and geometry of the die itself, the residence time in said element, and the ratio length of the die to diameter of the die influence the compression of the material thereby affecting the melt pressure. The die pressure depends on revolution, throughput and melt temperature and affects the viscosity and the release profile of the final product.

4. Temperature (Melt Zones)

The feeding cylinder should not be heated to prevent the starting material from melting in the feeder and causing an accumulation. The number of cylinders is variable, the longer the extruder the longer the residence time. The temperature of the cylinders (except feeding cylinder) destroys the material if it is too high: if too low the material does not sufficiently melt thereby resulting in an inhomogeneous mixture and degradation. The die temperature, if separately set too low, causes the "extrusion skin" to not properly form thereby making further processing of the extrudate difficult.

5. Revolution of the Extruder

If the extruder revolution speed is too high the material is stressed thereby affecting the viscosity and the release profile of the final product. If the extruder revolution speed is too low the load of the extruder is higher than 100% and the extruder shuts down automatically; and inter alia the residence time depends on the revolution.

6. Arrangement of Cylinders

The position of feeding cylinder and length of the extruder are important. The degassing should be located close to the feeder in order to avoid air pockets in the product; and if one of the components is thermo-labile it may be separately fed into one of the rear cylinders.

7. Temperature of the Water Cooling

Cooling of the engine and control of the temperature of the extrusion cylinders are important parameters.

The process according to the invention requires the use of suitable extruders, preferably screw extruders. Screw extruders which are equipped with two screws (twin-screw-extruders) are particularly preferred. Single-screw extruders are preferably excluded.

The extrusion is preferably performed so that the expansion of the strand due to extrusion is not more than 50%, i.e. that when using a die with a bore having a diameter of e.g. 6 mm, the extruded strand should have a diameter of not more than 9 mm. More preferably, the expansion of the strand is not more than 40%, still more preferably not more than 35%, most preferably not more than 30% and in particular not more than 25%. It has been surprisingly found that if the extruded material in the extruder is exposed to a mechanical stress exceeding a certain limit, a significant expansion of the strand occurs thereby resulting in undesirable irregularities of the properties of the extruded strand, particularly its mechanical properties.

For example, extrusion may be performed by means of a twin-screw-extruder type Micro 27 GL 40 D (Leistritz, Nürnberg, Germany), screw diameter 18 mm. Screws having eccentric ends may be used. A heatable die with a round bore having a diameter of 8 mm may be used. The entire extrusion process may be performed under nitrogen atmosphere. The extrusion parameters may be adjusted e.g. to the following values: rotational speed of the screws: 100 Upm; delivery rate: 4 kg/h; product temperature: 125° C.; and jacket temperature: 120° C.

After extrusion of the molten mixture and optional cooling of the extruded strand or extruded strands, the extrudates are preferably singulated. This singulation may preferably be performed by cutting up the extrudates by means of revolving or rotating knives, water jet cutters, wires, blades or with the assistance of laser cutters.

An inert gas atmosphere is not necessary for intermediate or final storage of the optionally singulated extrudate or the final shape of the dosage form according to the invention.

The singulated extrudate may be pelletized with conventional methods or be press-molded into tablets in order to impart the final shape to the dosage form. It is, however, also possible not to singulate the extruded strands and, with the assistance of contrarotating calender rolls comprising opposing recesses in their outer sleeve, to form them into the final shape, preferably a tablet, and to singulate these by conventional methods.

Should the optionally singulated extrudate not immediately be formed into the final shape, but instead cooled for storage, after the period of storage an inert gas atmosphere, preferably a nitrogen atmosphere, may optionally be provided and may be maintained during heating of the stored extrudate up until plasticization and definitive shaping to yield the dosage form.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a dosage form with a breaking strength of at least 500 N, may be established by simple preliminary testing.

The process according to the invention involves the extrusion of a composition comprising components (A), (C), optionally (B) and optionally (D). Preferably, extrusion is performed by means of twin-screw-extruders.

It has been surprisingly found that extrudates exhibiting an advantageous morphology are obtainable by means of twin-screw-extruders. It has been found that under suitable conditions the extrudate is surrounded by a shell which may be denoted as "extrusion skin". Said extrusion skin can be regarded as a collar-like or tubular structure forming a circumferential section of the extrudate about its longitudinal extrusion axis so that the outer surface of said collar-like or tubular structure forms the closed shell of the extrudate. Usually, only the front faces of the extrudate are not covered by said extrusion skin.

The extrusion skin surrounds the core of the extrudate in a collar-like or tubular arrangement and preferably is connected therewith in a seamless manner. The extrusion skin differs from said core in its morphology. Usually, the extrusion skin is visible with the naked eye in the cross-section of the extrudate, optionally by means of a microscope, since due to the different morphology of the material forming the extrusion skin and the material forming the core, the optical properties differ as well. It seems that during extrusion the material forming the extrusion skin is exposed to mechanical and thermal conditions differing from the conditions the core of the extrudate is exposed to. In consequence, a heterogeneous morphology of the extruded strand is obtained, which e.g. assumes radial symmetry when an extrusion die having circular shape is used. The material forming the extrusion skin and the material forming the core are usually distinguished by their morphology, preferably, however, not by their composition, particularly not by the relative content of components (A), (C), optionally (B) and optionally (D).

Usually the extrusion skin covers the entire shell of the extrudate like a one-piece collar, independently of what geometry has been chosen for the extrusion die. Therefore, the extrudate may assume circular, elliptic or other cross-sections.

The extrusion skin is preferably characterized by a unitary thickness. Preferably, the thickness of the extrusion skin is within the range from 0.1 to 4.0 mm, more preferably 0.15 to 3.5 mm, still more preferably 0.2 to 3.0 mm, most preferably 0.2 to 2.5 mm and in particular 0.2 to 2.0 mm. In a preferred embodiment the thickness of the extrusion skin in the sum over both opposing sides amounts to 0.5 to 50%, more preferably 1.0 to 40%, still more preferably 1.5 to 35%, most preferably 2.0 to 30% and in particular 2.5 to 25% of the diameter of the extrudate.

FIG. 1 shows a schematic view of extrudate (71) having a collar-like extrusion skin (72) entirely surrounding the core (73) about the longitudinal extrusion axis (74). The outer surface of extrusion skin (72) forms the shell (75) of the extrudate (71).

It has been surprisingly found that extrudates having an extrusion skin exhibit beneficial mechanical properties. They are particularly suitable as intermediates in the production of the dosage forms according to the invention, because they may be advantageously processed, in particular by singulating and/or forming.

When the dosage forms according to the invention are prepared by means of extrusion processes which lead to intermediates having an extrusion skin as described above, the dosage forms obtained therefrom are preferably also characterized by a particular morphology.

In a preferred embodiment those regions, which have formed the extrusion skin in the extruded intermediate, are still visible with the naked eye, optionally by means of a microscope, in the cross-section of the dosage form. This is because usually by further processing the extrudate, particularly by singulating and/or shaping, the different nature and thereby also the different optical properties of the material forming the extrusion skin and the material forming the core are maintained. In the following, that domain of the dosage forms which has emerged from the extrusion skin in the course of further processing the extruded intermediate, will be denoted as "tubular domain".

Preferably, the dosage form according to the invention comprises a tubular domain and a core located therein. Preferably, the tubular domain is connected with the core in a seamless manner. Preferably the tubular domain as well as the core have substantially the same chemical composition, i.e. substantially the same relative content of components (A), (C), optionally (B) and optionally (D). The material forming the tubular domain has a morphology differing from the material forming the core. Usually, this different morphology is also expressed in terms of different optical properties, so that the tubular domain and the core are visible with the naked eye in the cross-section of the dosage form.

In case that the dosage form has been coated, e.g. by a film coating, the tubular domain is located between the film coating and the core.

Since the dosage form according to the invention may be obtained in different ways from the extrudate containing the extrusion skin (intermediate), the tubular domain may take different arrangements and extensions within the dosage form according to the invention. All arrangements have in common, however, that the tubular domain partially covers the surface of the core, but usually not its entire surface. Preferably, two opposing surfaces of the core are not, or at least not fully covered by the tubular domain. In other words, preferably the tubular domain has two openings/blanks on opposing sides.

The thickness of the tubular domain may be uniform. It is also possible, however, that in the course of the processing, i.e. due to the subsequent shaping (e.g. press-forming) of the extrudate, various sections of the extrusion skin are expanded or compressed differently thereby leading to a variation of the thickness of the tubular domain within the dosage form.

Preferably the thickness of the tubular domain is within the range from 0.1 to 4.0 mm, more preferably 0.15 to 3.5 mm, still more preferably 0.2 to 3.0 mm, most preferably 0.2 to 2.5 mm and in particular 0.2 to 2.0 mm.

Figure 2A:
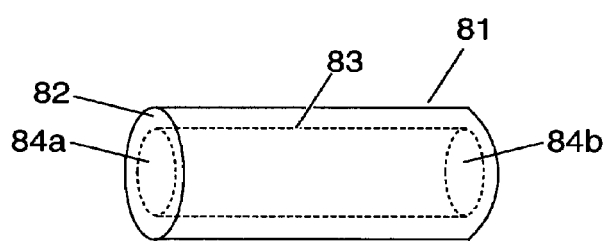
FIGS. 2A and 2B show schematic views of the preferred arrangements of the tubular domain within the dosage form.
Figure 2B:
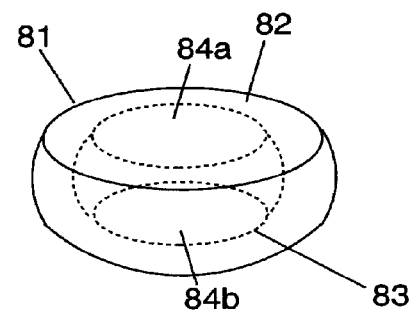

FIGS. 2A and 2B show schematic views of preferred arrangements of the tubular domain within the dosage form according to the invention. The dosage forms (81) contain a tubular domain (82) partially surrounding the core (83). The opposing surfaces (84a) and (84b) of the core (83), however, are not covered by the tubular domain (82).

The process for the preparation of the dosage form according to the invention is preferably performed continuously. Preferably, the process involves the extrusion of a homogeneous mixture of components (A), (C), optionally (B) and optionally (D). It is particularly advantageous if the obtained intermediate, e.g. the strand obtained by extrusion, exhibits uniform properties. Particularly desirable are uniform density, uniform distribution of the active substance, uniform mechanical properties, uniform porosity, uniform appearance of the surface, etc. Only under these circumstances the uniformity of the pharmacological properties, such as the stability of the release profile, may be ensured and the amount of rejects can be kept low.

Preferably, the process according to the present invention may be performed with less than 25% rejects, more preferably less than 20%, most preferably less than 15% and in particular less than 10% rejects, wherein the criteria for rejection are the FDA standards regarding the intervariability of the content of component (A), its release profile and/or the density of the dosage form when comparing two dosage forms, preferably taken from the same batch.

It has been surprisingly found that the above properties may be obtained by means of twin-screw-extruders.

The process according to the invention preferably involves the extrusion of a mixture of components (A), (C), optionally (B) and optionally (D), preferably by means of a twin-screw-extruder. After extrusion the extrudate is preferably singulated, shaped and optionally coated in order to obtain the final dosage form.

In a preferred embodiment of the process according to the invention, shaping is performed in the plasticized state of the mixture of components (A), (C), optionally (B) and optionally (D). It has been surprisingly found that the extrusion of certain polymers (C), particular of high molecular weight polyethylene oxides, yields intermediates exhibiting some kind of memory effect: when the singulated extrudates are shaped at ambient temperature, e.g. by press-forming, dosage forms are obtained which tend to regain their original outer form upon storage under stressed storage conditions, i.e. they return to the form they had prior to shaping.

The shape of the dosage form upon storage at stressed conditions, e.g. at 40° C./75% RH, may also be unstable for other reasons.

Said memory effect significantly deteriorates the storage stability of the dosage form, as by regaining its outer form several properties of the dosage form are changed. The same applies to any changes of the outer form due to other reasons.

It has been found that, for example, depending on the extrusion conditions a significant expansion of the strand may occur thereby resulting in an increase of the volume of the extrudate, i.e. a decrease of its density. Said expansion may be compensated by subsequently press-forming the singulated extrudate at a sufficient pressure, since under these conditions the expansion of the material may be reversed.

However, if press-forming has been performed at ambient temperature, the memory effect of the compressed extrudate will cause it to swell and to expand upon storage, thereby significantly increasing the volume of the dosage form.

It has been surprisingly found that such memory effect may be suppressed if shaping of the singulated extrudate is performed at increased temperature, i.e. in the plasticized state of the mixture of components (A), (C), optionally (B) and optionally (D). Preferably, shaping is performed at a pressure of at least 1 kN, more preferably within the range from 2 kN to 50 kN, e.g. by means of a tablet press. Preferably, shaping is performed at a temperature which preferably is about 40° C., more preferably about 30° C. and in particular about 25° C. below the melting range of the mixture of components (A), (C), optionally (B) and optionally (D). The melting range of a given mixture may be determined by conventional methods, preferably by DSC (e.g. with a DSC model 2920 (TA Instruments, New Castle) and ultrahigh pure nitrogen as purge gas at a flow rate of 150 ml/min; approximate sample weight of 10-20 mg, sealed in nonhermetic aluminium pans; temperature ramp speed 10° C./min).

In a preferred embodiment the outer shape of the dosage form according to the invention does not substantially change when being stored for at least 12 h, preferably for at least 24 h, at 40° C. and 75% RH, preferably in an open container.

In a preferred embodiment the volume of the dosage form according to the invention increases by not more than 20% or 17.5%, more preferably not more than 15% or 12.5%, still more preferably not more than 10% or 7.5%, most preferably not more than 6.0%, 5.0% or 4.0% and in particular not more than 3.0%, 2.0% or 1.0% when being stored for at least 12 h, preferably for at least 24 h, at a temperature of 20° C. below the melting range of the mixture of components (A), (C), optionally (B) and optionally (D), optionally at a temperature of 40° C. and 75% RH.

In a further preferred embodiment, the dosage form according to the invention assumes the form of a tablet, a capsule or is in the form of an oral osmotic therapeutic system (OROS), preferably if at least one further abuse-preventing component (a)-(f) is also present.

If components (c) and/or (d) and/or (f) are present in the dosage form according to the invention, care must be taken to ensure that they are formulated in such a manner or are present in such a low dose that, when correctly administered, the dosage form is able to bring about virtually no effect which impairs the patient or the efficacy of the active ingredient.

If the dosage form according to the invention contains component (d) and/or (f), the dosage must be selected such that, when correctly orally administered, no negative effect is caused. If, however, the intended dosage of the dosage form is exceeded in the event of abuse, nausea or an inclination to vomit or a bad flavor are produced. The particular quantity of component (d) and/or (f) which can still be tolerated by the patient in the event of correct oral administration may be determined by the person skilled in the art by simple preliminary testing.

If, however, irrespective of the fact that the dosage form according to the invention is virtually impossible to pulverize, the dosage form containing the components (c) and/or (d) and/or (f) is provided with protection, these components should preferably be used at a dosage which is sufficiently high that, when abusively administered, they bring about an intense negative effect on the abuser. This is preferably achieved by spatial separation of at least the active ingredient or active ingredients from components (c) and/or (d) and/or (f), wherein the active ingredient or active ingredients is/are present in at least one subunit (X) and components (c) and/or (d) and/or (f) is/are present in at least one subunit (Y), and wherein, when the dosage form is correctly administered, components (c), (d) and (f) do not exert their effect on taking and/or in the body and the remaining components of the formulation, in particular component (C) and optionally (D), are identical.

If the dosage form according to the invention comprises at least 2 of components (c) and (d) or (f), these may each be present in the same or different subunits (Y). Preferably, when present, all the components (c) and (d) and (f) are present in one and the same subunit (Y).

For the purposes of the present invention, subunits are solid formulations, which in each case, apart from conventional auxiliary substances known to the person skilled in the art, contain the active ingredient(s), at least one polymer (C) and the optionally present component (D) and optionally at least one of the optionally present components (a) and/or (b) and/or (e) or in each case at least one polymer (C) and optionally (D) and the antagonist(s) and/or emetic(s) and/or component (e) and/or component (f) and optionally at least one of the optionally present components (a) and/or (b). Care must here be taken to ensure that each of the subunits is formulated in accordance with the above-stated process.

One substantial advantage of the separated formulation of active ingredients from components (c) or (d) or (f) in subunits (X) and (Y) of the dosage form according to the invention is that, when correctly administered, components (c) and/or (d) and/or (f) are hardly released on taking and/or in the body or are released in such small quantities that they exert no effect which impairs the patient or therapeutic success or, on passing through the patient's body, they are only liberated in locations where they cannot be sufficiently absorbed to be effective. When the dosage form is correctly administered, preferably hardly any of components (c) and/or (d) and/or (f) is released into the patient's body or they go unnoticed by the patient.

The person skilled in the art will understand that the above-stated conditions may vary as a function of the particular components (c), (d) and/or (f) used and of the formulation of the subunits or the dosage form. The optimum formulation for the particular dosage form may be determined by simple preliminary testing. What is vital is that each subunit contains the polymer (C) and optionally component (D) and has been formulated in the above-stated manner.

Should, contrary to expectations, the abuser succeed in comminuting such a dosage form according to the invention, which comprises components (c) and/or (e) and/or (d) and/or (f) in subunits (Y), for the purpose of abusing the active ingredient and obtain a powder which is extracted with a suitable extracting agent, not only the active ingredient but also the particular component (c) and/or (e) and/or (f) and/or (d) will be obtained in a form in which it cannot readily be separated from the active ingredient, such that when the dosage form which has been tampered with is administered, in particular by oral and/or parenteral administration, it will exert its effect on taking and/or in the body combined with an additional negative effect on the abuser corresponding to component (c) and/or (d) and/or (f) or, when the attempt is made to extract the active ingredient, the coloration will act as a deterrent and so prevent abuse of the dosage form.

A dosage form according to the invention, in which the active ingredient or active ingredients is/are spatially separated from components (c), (d) and/or (e), preferably by formulation in different subunits, may be formulated in many different ways, wherein the corresponding subunits may each be present in the dosage form according to the invention in any desired spatial arrangement relative to one another, provided that the above-stated conditions for the release of components (c) and/or (d) are fulfilled.

The person skilled in the art will understand that component(s) (a) and/or (b) which are optionally also present may preferably be formulated in the dosage form according to the invention both in the particular subunits (X) and (Y) and in the form of independent subunits corresponding to subunits (X) and (Y), provided that neither the abuse-proofing nor the active ingredient release in the event of correct administration is impaired by the nature of the formulation and the polymer (C) and optionally (D) is included in the formulation and formulation is carried out in accordance with the above-stated process in order to achieve the necessary hardness.

In a preferred embodiment of the dosage form according to the invention, subunits (X) and (Y) are present in multiparticulate form, wherein microtablets, microcapsules, micropellets, granules, spheroids, beads or pellets are preferred and the same form, i.e. shape, is selected for both subunit (X) and subunit (Y), such that it is not possible to separate subunits (X) from (Y) by mechanical selection. The multiparticulate forms are preferably of a size in the range from 0.1 to 3 mm, preferably of 0.5 to 2 mm.

The subunits (X) and (Y) in multiparticulate form may also preferably be packaged in a capsule or be pressed into a tablet, wherein the final formulation in each case proceeds in such a manner that the subunits (X) and (Y) are also retained in the resultant dosage form.

The multiparticulate subunits (X) and (Y) of identical shape should also not be visually distinguishable from one another so that the abuser cannot separate them from one another by simple sorting. This may, for example, be achieved by the application of identical coatings which, apart from this disguising function, may also incorporate further functions, such as, for example, controlled release of one or more active ingredients or provision of a finish resistant to gastric juices on the particular subunits.

The multiparticulate subunits may also be formulated as an oral dosage form as a slurry or suspension in pharmaceutically safe suspending media.

In a further preferred embodiment of the present invention, subunits (X) and (Y) are in each case arranged in layers relative to one another.

The layered subunits (X) and (Y) are preferably arranged for this purpose vertically or horizontally relative to one another in the dosage form according to the invention, wherein in each case one or more layered subunits (X) and one or more layered subunits (Y) may be present in the dosage form, such that, apart from the preferred layer sequences (X)-(Y) or (X)-(Y)-(X), any desired other layer sequences may be considered, optionally in combination with layers containing components (a) and/or (b).

Another preferred dosage form according to the invention is one in which subunit (Y) forms a core which is completely enclosed by subunit (X), wherein a separation layer (Z) may be present between said layers. Such a structure is preferably also suitable for the above-stated multiparticulate forms, wherein both subunits (X) and (Y) and an optionally present separation layer (Z), which must satisfy the hardness requirement according to the invention, are formulated in one and the same multiparticulate form. In a further preferred embodiment of the dosage form according to the invention, the subunit (X) forms a core, which is enclosed by subunit (Y), wherein the latter comprises at least one channel which leads from the core to the surface of the dosage form.

The dosage form according to the invention may comprise, between one layer of the subunit (X) and one layer of the subunit (Y), in each case one or more, preferably one, optionally swellable separation layer (Z) which serves to separate subunit (X) spatially from (Y).

If the dosage form according to the invention comprises the layered subunits (X) and (Y) and an optionally present separation layer (Z) in an at least partially vertical or horizontal arrangement, the dosage form preferably takes the form of a tablet, a coextrudate or a laminate.

In one particularly preferred embodiment, the entirety of the free surface of subunit (Y) and optionally at least part of the free surface of subunit(s) (X) and optionally at least part of the free surface of the optionally present separation layer(s) (Z) may be coated with at least one barrier layer (Z') which prevents release of component (c) and/or (e) and/or (d) and/or (f). The barrier layer (Z') must also fulfill the hardness conditions according to the invention.

Another particularly preferred embodiment of the dosage form according to the invention comprises a vertical or horizontal arrangement of the layers of subunits (X) and (Y) and at least one push layer (p) arranged therebetween, and optionally a separation layer (Z), in which dosage form the entirety of the free surface of layer structure consisting of subunits (X) and (Y), the push layer and the optionally present separation layer (Z) is provided with a semipermeable coating (E), which is permeable to a release medium, i.e. conventionally a physiological liquid, but substantially impermeable to the active ingredient and to component (c) and/or (d) and/or (f), and wherein this coating (E) comprises at least one opening for release of the active ingredient in the area of subunit (X).

A corresponding dosage form is known to the person skilled in the art, for example under the name oral osmotic therapeutic system (OROS), as are suitable materials and methods for the production thereof, inter alia from U.S. Pat. No. 4,612,008, U.S. Pat. No. 4,765,989 and U.S. Pat. No. 4,783,337. The disclosure of these references is expressly incorporated herein and made a part of this present application.

In a further preferred embodiment, the subunit (X) of the dosage form according to the invention is in the form of a tablet, the edge face of which and optionally one of the two main faces is covered with a barrier layer (Z') containing component (c) and/or (d) and/or (f).

The person skilled in the art will understand that the auxiliary substances of the subunit(s) (X) or (Y) and of the optionally present separation layer(s) (Z) and/or of the barrier layer(s) (Z') used in formulating the dosage form according to the invention will vary as a function of the arrangement thereof in the dosage form according to the invention, the mode of administration and as a function of the particular active ingredient of the optionally present components (a) and/or (b) and/or (e) and of component (c) and/or (d) and/or (f). The materials which have the requisite properties are in each case known per se to the person skilled in the art.

If release of component (c) and/or (d) and/or (f) from subunit (Y) of the dosage form according to the invention is prevented with the assistance of a cover, preferably a barrier layer, the subunit may consist of conventional materials known to the person skilled in the art, providing that it contains at least one polymer (C) and optionally (D) to fulfill the hardness condition of the dosage form according to the invention.

If a corresponding barrier layer (Z') is not provided to prevent release of component (c) and/or (d) and/or (f), the materials of the subunits should be selected such that release of the particular component (c) and/or (d) from subunit (Y) is virtually ruled out. The materials which are stated below to be suitable for production of the barrier layer may preferably be used for this purpose.

Preferred materials are those which are selected from the group comprising alkylcelluloses, hydroxyalkyl-celluloses, glucans, scleroglucans, mannans, xanthans, copolymers of poly[bis(p-carboxyphenoxy)propane and sebacic acid, preferably in a molar ratio of 20:80 (commercially available under the name Polifeprosan 20®), carboxymethylcelluloses, cellulose ethers, cellulose esters, nitrocelluloses, polymers based on (meth)acrylic acid and the esters thereof, polyamides, polycarbonates, polyalkylenes, polyalkylene glycols, polyalkylene oxides, polyalkylene terephthalates, polyvinyl alcohols, polyvinyl ethers, polyvinyl esters, halogenated polyvinyls, polyglycolides, polysiloxanes and polyurethanes and the copolymers thereof.

Particularly suitable materials may be selected from the group comprising methylcellulose, ethylcellulose, hydroxypropylcellulose, hydroxypropylmethylcellulose, hydroxybutylmethylcellulose, cellulose acetate, cellulose propionate (of low, medium or high molecular weight), cellulose acetate propionate, cellulose acetate butyrate, cellulose acetate phthalate, carboxymethylcellulose, cellulose triacetate, sodium cellulose sulfate, polymethyl methacrylate, polyethyl methacrylate, polybutyl methacrylate, polyisobutyl methacrylate, polyhexyl methacrylate, polyisodecyl methacrylate, polylauryl methacrylate, polyphenyl methacrylate, polymethyl acrylate, polyisopropyl acrylate, polyisobutyl acrylate, polyoctadecyl acrylate, polyethylene, low density polyethylene, high density polyethylene, polypropylene, polyethylene glycol, polyethylene oxide, polyethylene terephthalate, polyvinyl alcohol, polyvinyl isobutyl ether, polyvinyl acetate and polyvinyl chloride.

Particularly suitable copolymers may be selected from the group comprising copolymers of butyl methacrylate and isobutyl methacrylate, copolymers of methyl vinyl ether and maleic acid with high molecular weight, copolymers of methyl vinyl ether and maleic acid monoethyl ester, copolymers of methyl vinyl ether and maleic anhydride and copolymers of vinyl alcohol and vinyl acetate.

Further materials which are particularly suitable for formulating the barrier layer are starch-filled polycaprolactone (WO98/20073), aliphatic polyesteramides (DE 19 753 534 A1, DE 19 800 698 A1, EP 0 820 698 A1), aliphatic and aromatic polyester urethanes (DE 19822979), polyhydroxyalkanoates, in particular polyhydroxybutyrates, polyhydroxyvalerates, casein (DE 4 309 528), polylactides and copolylactides (EP 0 980 894 A1). The disclosure of these references is expressly incorporated herein and made a part of this present application.

The above-stated materials may optionally be blended with further conventional auxiliary substances known to the person skilled in the art, preferably selected from the group comprising glyceryl monostearate, semi-synthetic triglyceride derivatives, semi-synthetic glycerides, hydrogenated castor oil, glyceryl palmitostearate, glyceryl behenate, polyvinyl-pyrrolidone, gelatine, magnesium stearate, stearic acid, sodium stearate, talcum, sodium benzoate, boric acid and colloidal silica, fatty acids, substituted triglycerides, glycerides, polyoxyalkylene glycols and the derivatives thereof.

If the dosage form according to the invention comprises a separation layer (Z'), said layer, like the uncovered subunit (Y), may preferably consist of the above-stated materials described for the barrier layer. The person skilled in the art will understand that release of the active ingredient or of component (c) and/or (d) from the particular subunit may be controlled by the thickness of the separation layer.

The dosage form according to the invention exhibits controlled release of the active ingredient. It is preferably suitable for twice daily administration to patients.

The release properties of the dosage form according to the invention are substantially independent from the pH value of the release medium, i.e. preferably the release profile in artificial intestinal juice substantially corresponds to the release profile in artificial gastric juice. Preferably, at any given time point the release profiles deviate from one another by not more than 20%, more preferably not more than 15%, still more preferably not more than 10%, yet more preferably not more than 7.5%, most preferably not more than 5.0% and in particular not more than 2.5%.

Preferably, the dosage form according to the invention exhibits a uniform release profile. Preferably, the release profile of the active substance with abuse potential (A) is inter-individually uniform (i.e. when comparing dosage forms obtained from the same process) and/or uniform within a single dosage form (i.e. when comparing segments of the same dosage form). Preferably, when comparing two probes each having a mass of preferably 500 mg, the total amount of the released active substance for any given time point of the measurement does not deviate by more than 20%, more preferably not more than 15%, still more preferably not more than 10%, yet more preferably not more than 7.5%, most preferably not more than 5.0% and in particular not more than 2.5%.

Preferably, the release profile of the dosage form according to the present invention is stable upon storage, preferably upon storage at elevated temperature, e.g. 37° C., for 3 month in sealed containers. In this regard "stable" means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

The dosage form according to the invention may comprise one or more active ingredients at least partially in controlled release form, wherein controlled release may be achieved with the assistance of conventional materials and methods known to the person skilled in the art, for example by embedding the active ingredient in a controlled release matrix or by the application of one or more controlled release coatings. Active ingredient release must, however, be controlled such that the above-stated conditions are fulfilled in each case, for example that, in the event of correct administration of the dosage form, the active ingredient or active ingredients are virtually completely released before the optionally present component (c) and/or (d) can exert an impairing effect. Addition of materials effecting controlled release must moreover not impair the necessary hardness.

Controlled release from the dosage form according to the invention is preferably achieved by embedding the active ingredient in a matrix. The auxiliary substances acting as matrix materials control active ingredient release. Matrix materials may, for example, be hydrophilic, gel-forming materials, from which active ingredient release proceeds mainly by diffusion, or hydrophobic materials, from which active ingredient release proceeds mainly by diffusion from the pores in the matrix.

Physiologically acceptable, hydrophobic materials which are known to the person skilled in the art may be used as matrix materials. Polymers, particularly preferably cellulose ethers, cellulose esters and/or acrylic resins are preferably used as hydrophilic matrix materials. Ethylcellulose, hydroxypropylmethylcellulose, hydroxypropylcellulose, hydroxymethylcellulose, poly(meth)acrylic acid and/or the derivatives thereof, such as the salts, amides or esters thereof are very particularly preferably used as matrix materials.

Matrix materials prepared from hydrophobic materials, such as hydrophobic polymers, waxes, fats, long-chain fatty acids, fatty alcohols or corresponding esters or ethers or mixtures thereof are also preferred. Mono- or diglycerides of C12-C30 fatty acids and/or C12-C30 fatty alcohols and/or waxes or mixtures thereof are particularly preferably used as hydrophobic materials.

It is also possible to use mixtures of the above-stated hydrophilic and hydrophobic materials as matrix materials.

Component (C) and the optionally present component (D), which serve to achieve the breaking strength of at least 500 N which is necessary according to the invention may furthermore also optionally serve as additional matrix materials.

If the dosage form according to the invention is intended for oral administration, it may also preferably comprise a coating which is resistant to gastric juices and dissolves as a function of the pH value of the release environment. By means of this coating, it is possible to ensure that the dosage form according to the invention passes through the stomach undissolved and the active ingredient is only released in the intestines. The coating which is resistant to gastric juices preferably dissolves at a pH value of between 5 and 7.5.

Corresponding materials and methods for the controlled release of active ingredients and for the application of coatings which are resistant to gastric juices are known to the person skilled in the art, for example from "Coated Pharmaceutical Dosage Forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers. The disclosure of these references is expressly incorporated herein and made a part of this present application.

Method for Determining the Breaking Strength

In order to verify whether a polymer may be used as component (C) or (D), the polymer is pressed to form a tablet with a diameter of 10 mm and a height of 5 mm using a force of 150 N at a temperature which at least corresponds to the softening point of the polymer and is determined with the assistance of a DSC diagram of the polymer. Using tablets produced in this manner, breaking strength is determined with the apparatus described below in accordance with the method for determining the breaking strength of tablets published in the European Pharmacopoeia 1997, page 143-144, method no. 2.9.8. The apparatus used for the measurement is a "Zwick Z 2.5" materials tester, Fmax=2.5 kN with a maximum draw of 1150 mm, which should be set up with 1 column and 1 spindle, a clearance behind of 100 mm and a test speed adjustable between 0.1 and 800 mm/min together with testControl software. Measurement is performed using a pressure piston with screw-in inserts and a cylinder (diam. 10 mm), a force transducer, Fmax. 1 kN, diameter=8 mm, class 0.5 from 10 N, class 1 from 2 N to ISO 7500-1, with manufacturer's test certificate M to DIN 55350-18 (Zwick gross force Fmax=1.45 kN) (all apparatus from Zwick GmbH & Co. KG, Ulm, Germany) with order no. BTC-FR 2.5 TH. D09 for the tester, order no. BTC-LC 0050N. P01 for the force transducer, order no. BO 70000 S06 for the centering device.

Figure 3:
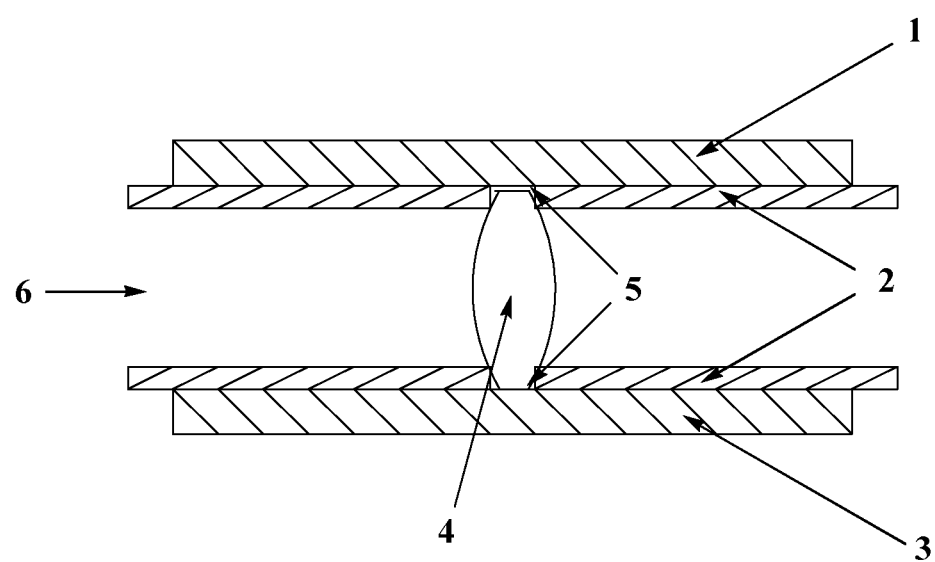
FIG. 3 shows the measurement of the breaking strength of a tablet.

FIG. 3 shows the measurement of the breaking strength of a tablet, in particular the tablet (4) adjustment device (6) used for this purpose before and during the measurement. To this end, the tablet (4) is held between the upper pressure plate (1) and the lower pressure plate (3) of the force application apparatus (not shown) with the assistance of two 2-part clamping devices, which are in each case firmly fastened (not shown) with the upper and lower pressure plate once the spacing (5) necessary for accommodating and centering the tablet to be measured has been established. The spacing (5) may be established by moving the 2-part clamping devices horizontally outwards or inwards in each case on the pressure plate on which they are mounted.

The tablets deemed to be resistant to breaking under a specific load include not only those which have not broken but also those which may have suffered plastic deformation under the action of the force.

In the case of the dosage forms according to the invention, breaking strength is determined in accordance with the stated method, dosage forms other than tablets also being tested.

The following Examples illustrate the invention purely by way of example and without restricting the general concept of the invention.

EXAMPLE 1

| Components | Per tablet | Per batch |
|---|---|---|
| Tramadol HCl | 100.0 mg | 1495.0 g |
| Polyethylene oxide, NF, MW 7 000 000 (Polyox WSR 303, Dow Chemicals) | 167.8 mg | 2508.6 g |
| Hydroxypropylmethylcellulose 100 000 mPa · s | 33.5 mg | 500.8 g |
| Polyethylene glycol (PEG 6000) | 33.5 mg | 500.8 g |
| Butylhydroxytoluene (BHT) | 0.2 mg | 3.0 g |
| Total weight | 335.0 mg | 5008.2 g |

The stated quantity of BHT was dissolved in ethanol (96%), such that a 7.7% (mass/mass) ethanolic solution was obtained. This was mixed initially with 150 g of polyethylene oxide in a high speed mixer for 30 minutes and then the remaining quantity of polyethylene oxide was added and stirring continued for a further 30 minutes. The composition was dried for 12 h at 40° C. All the further components were added and mixed for 15 min in a free-fall mixer. The powder mixture was apportioned into an extruder. Extrusion was performed using a model Micro 27 GL 40 D double screw extruder with a spindle diameter of 18 mm manufactured by Leistritz (Nürnberg). Screws with blunt ends were used, the hex socket at the end of the screws being closed with a cap. The die used is a heatable round die with a diameter of 8 mm. The entire process was performed under an $N_2$ atmosphere.

The following parameters were selected for extrusion:

| Screw speed: | 100 rpm |
|---|---|
| Throughput: | 4 kg/h |
| Product temperature: | 125° C. |
| Casing temperature: | 120° C. |

The extrudate, which was still hot, was cooled under a nitrogen atmosphere. The cooled strand was singulated into biplanar tablets. The tablets did not break when exposed to a force of 500 N. The tablets could not be comminuted either with a hammer or with the assistance of a mortar and pestle.

The color of the cooled strand or of the 10 tablets singulated therefrom was determined at N 9.5/using the Munsell Book of Color, such that the dosage form produced by the process according to the invention did not exhibit any discoloration due to the thermoforming with the assistance of an extruder.

EXAMPLE 2

| Components | Per Tablet | Per batch | |
|---|---|---|---|
| Oxycodon HCl | 20.0 mg | 410.1 g | 13.7% |
| Polyethylene oxide 7 000 000 (Polyox WSR 303, DOW Chemicals) | 107.2 mg | 2199.3 g | 73.2% |
| Polyethylene glycol (PEG 6000) | 15.0 mg | 307.8 g | 10.3% |
| Hypromellose (Metholose 90 SH 100 000 cP, ShinEtsu) | 3.8 mg | 76.8 g | 2.6% |
| α-Tocopherol | 0.2 mg | 3.0 g | 0.1% |
| Aerosil (highly disperse $SiO_2$) | 0.2 mg | 3.0 g | 0.1% |
| | 146.4 mg | 3000.0 g | 100% |

50 g of the polyethylene oxide, 3 g α-tocopherol and 3 g Aerosil were mixed to a homogeneous mixture by means of a mortar. All the further components were added and mixed for 15 minutes in a free-fall mixer.

Extrusion was performed using a model Micro 27 PH 40 D twin screw extruder manufactured by Leistritz (Nürnberg). Screws having eccentric ends were used. The die used is a heatable round die having a diameter of 9 mm.

The following parameters were selected for extrusion:

| Screw speed: | 100 rpm |
|---|---|
| Throughput: | 4 kg/h |
| Product temperature: | 134° C. |
| Casing temperature: | heating zones 1 to 10: 100° C. |
| | heating zone 11 (die): 120° C. |

The extrudate, which was still hot, was cooled. No nitrogen atmosphere was used. The product did not exhibit any yellowish discoloration.

The cooled strand was singulated into biplanar slices. The final press-forming was performed by means on an eccentric tablet press (model EK0). Oblong punches (width 5 mm, length 12 mm) were used as tabletting tool. The respective tablets (mass and form) were punched from the slices and press-formed. One tablet was obtained from one slice.

The breaking strength of the tablets was determined with the stated apparatus in accordance with the stated method. The tablets did not crush when exposed to a force of 500 N. The tablet could not be comminuted with a hammer. This could not be achieved with the assistance of a pestle and mortar either.

In vitro release of the active ingredient from the preparation was determined in a paddle stirrer apparatus with sinker in accordance with Pharm. Eur. The temperature of the release medium was 37° C. and the rotational speed of the stirrer 75 min$^{-1}$. 600 ml of artificial intestinal juice, pH 6.8 were used as release medium. The released quantity of active ingredient present in the dissolution medium at each point in time was determined by spectrophotometry.

| Time | Amount Released |
|---|---|
| 60 min | 36% |
| 240 min | 79% |
| 480 min | 99% |
| 720 min | 107% |

EXAMPLE 3

| Components | Per Tablet | Per batch | % |
|---|---|---|---|
| Oxycodon HCl | 20.0 mg | 333.3 g | 11.1 |
| Polyethylene oxide 7 000 000 (Polyox WSR 303, DOW Chemicals) | 122.6 mg | 2060.7 g | 68.7 |
| Polyethylene glycol (PEG 6000) | 18.0 mg | 300.0 g | 10.0 |
| Hypromellose (Metholose 90 SH 100 000 cP, ShinEtsu) | 18.0 mg | 300.0 g | 10.0 |
| α-Tocopherol | 0.2 mg | 3.0 g | 0.1 |
| Aerosil (highly disperse SiO$_2$) | 0.2 mg | 3.0 g | 0.1 |
| | 180 mg | 3000.0 g | 100% |

50 g of the polyethylene oxide, 3 g α-tocopherol and 3 g Aerosil were mixed to a homogeneous mixture by means of a mortar. All the further components were added and mixed for 15 minutes in a free-fall mixer.

Extrusion was performed using a model Micro 27 PH 40 D twin screw extruder manufactured by Leistritz (Nürnberg). Screws having eccentric ends were used. The die used is a heatable round die having a diameter of 9 mm.

The following parameters were selected for extrusion:

| Screw speed: | 100 rpm |
|---|---|
| Throughput: | 4 kg/h |
| Product temperature: | 134° C. |
| Casing temperature: | heating zones 1 to 10: 100° C. |
| | heating zone 11 (die): 120° C. |

The extrudate, which was still hot, was cooled. No nitrogen atmosphere was used. The product did not exhibit any yellowish discoloration.

The cooled strand was singulated into biplanar slices. The final press-forming was performed by means on an eccentric tablet press (model EK0). Oblong punches (width 5 mm, length 12 mm) were used as tabletting tool. The respective tablets (mass and form) were punched from the slices and press-formed. One tablet was obtained from one slice.

The breaking strength of the tablets was determined with the stated apparatus in accordance with the stated method. The tablets did not crush when exposed to a force of 500 N. The tablet could not be comminuted with a hammer. This could not be achieved with the assistance of a pestle and mortar either.

In vitro release of the active ingredient from the preparation was determined in a paddle stirrer apparatus with sinker in accordance with Pharm. Eur. The temperature of the release medium was 37° C. and the rotational speed of the stirrer 75 min$^{-1}$. 600 ml of artificial intestinal juice, pH 6.8 were used as release medium. The released quantity of active ingredient present in the dissolution medium at each point in time was determined by spectrophotometry.

| Time | Amount released |
|---|---|
| 60 min | 33% |
| 240 min | 76% |
| 480 min | 100% |
| 720 min | 108% |

EXAMPLE 4

| Components | Per tablet | Per batch | % |
|---|---|---|---|
| Tramadol | 116.5 mg | 349.0 g | 34.9 |
| Polyethylene oxide 7 000 000 (Polyox WSR 303, DOW Chemicals) | 150.2 mg | 450.0 g | 45.0 |
| Polyethylene glycol (PEG 6000) | 33.4 mg | 100.0 g | 10.0 |
| Hypromellose (Metholose 90 SH 100 000 cP, ShinEtsu) | 33.4 mg | 100.0 g | 10.0 |
| Butylhydroxytoluene | 0.3 mg | 1.0 g | 0.1 |
| | 333.8 mg | 1000 g | 100% |

45 g of the polyethylene oxide and 1 butylhydroxytoluene were mixed to a homogeneous mixture by means of a mortar. All the further components were added and mixed for 15 minutes in a free-fall mixer.

Extrusion was performed using a model Micro 27 PH 40 D twin screw extruder manufactured by Leistritz (Nürnberg). Screws having eccentric ends were used. The die used is a heatable round die having a diameter of 9 mm.

The following parameters were selected for extrusion:

| Screw speed: | 100 rpm |
|---|---|
| Throughput: | 4 kg/h |
| Product temperature: | 134° C. |
| Casing temperature: | heating zones 1 to 10: 100° C. |
| | heating zone 11 (die): 120° C. |

The extrudate, which was still hot, was cooled. No nitrogen atmosphere was used. The product did not exhibit any yellowish discoloration.

The cooled strand was singulated into biplanar slices. The final press-forming was performed by means on an eccentric tablet press (model EK0). Round punches (diameter 10 mm) having a radius of curvature of 8 mm were used as tabletting tool. One tablet was obtained from one slice.

The breaking strength of the tablets was determined with the stated apparatus in accordance with the stated method. The tablets did not crush when exposed to a force of 500 N. The tablet could not be comminuted with a hammer. This could not be achieved with the assistance of a pestle and mortar either.

EXAMPLE 5

| Components | Per Tablet | Per batch | % |
|---|---|---|---|
| Oxycodon HCl | 40.00 mg | 133.3 g | 13.3 |
| Polyethylene oxide 5 000 000 (Polyox WSR Coagulant, DOW Chemicals) | 190.00 mg | 643.3 g | 63.3 |
| Polyethylene glycol (PEG 6000) | 30.0 mg | 100.0 g | 10.0 |
| Hypromellose (Methocel 90 SH 100 000 cP, ShinEtsu) | 30.0 mg | 100.0 g | 10.0 |
| α-Tocopherol | 5.0 mg | 16.7 g | 1.7 |
| Aerosil (highly disperse SiO$_2$) | 5.0 mg | 16.7 g | 1.7 |
| | 300 mg | 1000 g | 100 |

50 g of the polyethylene oxide, 5 g α-tocopherol and 5 g Aerosil were mixed to a homogeneous mixture by means of a mortar. All the further components were added and mixed for 15 minutes in a free-fall mixer.

Extrusion was performed using a model Micro 27 PH 40 D twin screw extruder manufactured by Leistritz (Nürnberg). Screws having eccentric ends were used. The die used is a heatable round die having a diameter of 9 mm.

The following parameters were selected for extrusion:

| Screw speed: | 100 rpm |
|---|---|
| Throughput: | 4 kg/h |
| Product temperature: | 134° C. |
| Casing temperature: | heating zones 1 to 10: 100° C. |
| | heating zone 11 (die): 120° C. |

The extrudate, which was still hot, was cooled. No nitrogen atmosphere was used. The product exhibited a slight yellowish coloration. However, this coloration was merely caused by the natural color of α-tocopherol, but was not intensified by the extrusion, i.e. the extrusion was performed without discoloration.

The cooled strand was singulated into biplanar slices. The final press-forming was performed by means on an eccentric tablet press (model EK0). Round punches (diameter 10 mm) having a radius of curvature of 8 mm were used as tabletting tool. One tablet was obtained from one slice.

The breaking strength of the tablets was determined with the stated apparatus in accordance with the stated method. The tablets did not crush when exposed to a force of 500 N. The tablet could not be comminuted with a hammer. This could not be achieved with the assistance of a pestle and mortar either.

In vitro release of the active ingredient from the preparation was determined in a paddle stirrer apparatus with sinker in accordance with Pharm. Eur. The temperature of the release medium was 37° C. and the rotational speed of the stirrer 75 min$^{-1}$. 600 ml of artificial intestinal juice, pH 6.8 were used as release medium. The released quantity of active ingredient present in the dissolution medium at each point in time was determined by spectrophotometry.

| Time | Amount released |
|---|---|
| 60 min | 33% |
| 240 min | 76% |
| 480 min | 100% |
| 720 min | 108% |

The invention claimed is:

1. An abuse-proofed dosage form thermoformed by extrusion without discoloration comprising one or more active ingredients with abuse potential (A), optionally physiologically acceptable auxiliary substances (B), at least one synthetic or natural polymer (C) and optionally at least one wax (D), wherein the dosage form exhibits a breaking strength of at least 500 N, the one or more active ingredients with abuse potential (A) are selected from the group consisting of hydromorphone and physiologically acceptable compounds and derivatives thereof, the polymer (C) comprises polyethylene oxide having a molecular weight of at least 0.5 million g/mol, and the content of polymer (C) is at least 30 wt. % relative to the total weight of the dosage form.

2. The dosage form according to claim 1, which is in the form of a tablet.

3. The dosage form according to claim 1, wherein the molecular weight of the polyethylene oxide (C) is at least 1 million.

4. The dosage form according to claim 3, wherein the molecular weight of the polyethylene oxide is in the range of from about 1 to about 15 million.

5. The dosage form according to claim 1, which contains the wax (D), and the wax (D) is at least one natural, semi-synthetic or synthetic wax with a softening point of at least 60° C.

6. The dosage form according to claim 5, wherein the wax (D) is carnauba wax or beeswax.

7. The dosage form according to claim 1, which additionally comprises
   (a) at least one substance which irritates the nasal passages and/or pharynx; and/or
   (b) at least one viscosity-increasing agent, which in the presence of an active ingredient extracted from the dosage form using a liquid medium, forms a gel with the extract obtained from the dosage form, which gel optionally remains visually distinguishable when introduced into a further quantity of an aqueous liquid; and/or
   (c) at least one antagonist for the active ingredient or active ingredients with abuse potential; and/or
   (d) at least one emetic; and/or
   (e) at least one dye; and/or
   (f) at least one bitter substance.

8. The dosage form according to claim 7, which comprises component (b), wherein component (b) is at least one viscosity-increasing agent selected from the group consisting of microcystalline cellulose combined with carboxymethylcellulose sodium, polyacrylic acid, locust bean flour, pectins, waxy maize starch, sodium alginate, guar flour, iota carrageen, karaya gum, gellan gum, galactomannan, tara bean flour, propylene glycol alginate, apple pectin, sodium hyaluronate, tragacanth, tara gum, fermeted polysaccharide welan gum, and xanthan gum.

9. The dosage form according to claim 7, which comprises component (c), wherein component (c) is at least one opioid antagonist selected from the group consisting of naloxone, naltrexone, nalmefene, nalid, nalmexone, nalorphine, naluphine and a corresponding physiologically acceptable compound, a base, and a salt thereof.

10. The dosage form according to claim 1, which contains at least one active ingredient with abuse potential (A) at least partially in controlled release form.

11. The dosage form according to claim 10, wherein each of the active ingredients with abuse potential (A) is present in a controlled release matrix.

12. The dosage form according to claim 11, wherein the controlled release matrix material comprises component (C) and/or the optionally present component (D).

13. The dosage form according to claim 1, which comprises a core and a tubular domain surrounding the core, wherein said tubular domain has a morphology different from that of the core.

14. The dosage form according to claim 13, wherein the core and the tubular domain have substantially the same chemical composition.

15. The dosage form according to claim 13, wherein the tubular domain does not completely cover the core.

16. The dosage form according to claim 1, which comprises a physiologically acceptable auxiliary substance (B), wherein the physiologically acceptable auxiliary substance (B) is an antioxidant.

17. The dosage form according to claim 16, wherein the antioxidant is selected from the group consisting of ascorbic acid, salts of ascorbic acid, butylhydroxyanisole, butylhydroxytoluene, monothioglycerol, phosphorous acid, vitamin C, vitamin E and the derivatives thereof, sodium bisulfate and α-tocopherol.

18. A process for the production of a dosage form according to claim 1, comprising
I) mixing components (A), the optionally present component (B), (C) and the optionally present component (D) and co-mixing or separately mixing the optionally present components (a) to (f) with the addition of component (C) and optionally (D) to form a resultant mixture or plurality of resultant mixtures;
II) heating the resultant mixture or the resultant mixtures in an extruder at least up to the softening point of component (C) and extruding the mixture as a plastic extrudate through an outlet orifice of the extruder by application of force; and
III) singulating and forming the still plastic extrudate into the dosage form; or
IV) cooling and forming the optionally reheated singulated extrudate into the dosage form.

19. The process according to claim 18, wherein process step II) is performed by means of a twin-screw-extruder.

20. The process according to claim 18, wherein process steps II) and III) and optionally process steps I) and IV) are performed under an inert gas atmosphere.

21. The process according to claim 20, wherein the inert gas atmosphere is nitrogen.

22. The process according to claim 18, wherein mixing of the components according to process step I) proceeds in the extruder under an inert gas atmosphere.

23. The process according to claim 18, wherein the mixtures according to process step I) are co-extruded or separately extruded.

24. The process according to claim 18, wherein the mixture or the mixtures according to process step I) are extruded through a die with at least one bore.

25. The process according to claim 18, wherein the extrudate is singulated by cutting.

26. The process according to claim 18, wherein the extrudate is in the form of a strand and is shaped and singulated with the assistance of counter rotating calender rolls comprising opposing recesses in their outer sleeve.

27. The process according to claim 18, wherein the singulated extrudate is pelletized or pressed into tablets.

28. The process according to claim 18, wherein swelling and expansion of the dosage form upon storage is suppressed by press forming the singulated extrudate at a pressure of at least 1 kN and a temperature of between 25° C. and 40° C. below the melting range of the mixture of the components.

29. The dosage form according to claim 1, wherein the physiologically acceptable compounds and derivatives are salts, solvates, esters, ethers, and amides.

* * * * *

UNITED STATES PATENT AND TRADEMARK OFFICE
CERTIFICATE OF CORRECTION

PATENT NO. : 9,629,807 B2
APPLICATION NO. : 15/132325
DATED : April 25, 2017
INVENTOR(S) : Arkenau-Maric et al.

It is certified that error appears in the above-identified patent and that said Letters Patent is hereby corrected as shown below:

In the Specification

Column 3, Line 37, "hot-met" -- should read -- hot-melt --.

Column 5, Line 25, "11μ-tet" -- should read -- 11β-tet --.

Column 12, Line 6, "D0210" -- should read -- D021® --.

Column 30, Line 65-66, "Núrnberg" -- should read -- Nürnberg --.

Signed and Sealed this
Twenty-fifth Day of June, 2019

Andrei Iancu
*Director of the United States Patent and Trademark Office*